United States Patent
Ambati et al.

(10) Patent No.: US 9,877,973 B2
(45) Date of Patent: Jan. 30, 2018

(54) INTRAOCULAR DRUG DELIVERY DEVICE AND ASSOCIATED METHODS

(71) Applicant: University of Utah Research Foundation, Salt Lake City, UT (US)

(72) Inventors: Balamurali K. Ambati, Salt Lake City, UT (US); Bruce K. Gale, Salt Lake City, UT (US); Srinivas Rao Chennamaneni, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 0 days.

(21) Appl. No.: 15/590,868

(22) Filed: May 9, 2017

(65) Prior Publication Data
US 2017/0239272 A1    Aug. 24, 2017

Related U.S. Application Data

(63) Continuation-in-part of application No. 15/391,666, filed on Dec. 27, 2016, which is a continuation-in-part of application No. 13/543,597, filed on Jul. 6, 2012, which is a continuation-in-part of application No. 13/211,169, filed on Aug. 16, 2011, now Pat. No. 9,095,404, which is a continuation-in-part of application No. 12/945,428, filed on Nov. 12, 2010, now Pat. No. 8,663,194, which is a continuation-in-part of application No. PCT/US2009/043566, filed on May 12, 2009.

(60) Provisional application No. 61/052,507, filed on May 12, 2008.

(51) Int. Cl.
*A61M 31/00* (2006.01)
*A61K 31/573* (2006.01)
*A61K 9/00* (2006.01)
*A61K 9/20* (2006.01)

(52) U.S. Cl.
CPC .......... *A61K 31/573* (2013.01); *A61K 9/0051* (2013.01); *A61K 9/204* (2013.01); *A61K 9/2054* (2013.01)

(58) Field of Classification Search
CPC .................................................. A61K 9/0051
USPC ........................................................ 424/428
See application file for complete search history.

(56) References Cited

U.S. PATENT DOCUMENTS

| | | | |
|---|---|---|---|
| 3,986,510 A | 10/1976 | Higuchi et al. | |
| 4,281,654 A | 8/1981 | Shell et al. | |
| 4,853,224 A | 8/1989 | Wong | |
| 4,863,457 A | 9/1989 | Lee | |
| 4,997,652 A | 3/1991 | Wong | |
| 5,098,443 A | 3/1992 | Parel et al. | |
| 5,183,662 A | 2/1993 | Morita et al. | |
| 5,185,152 A | 2/1993 | Peyman | |
| 5,330,768 A | 7/1994 | Park et al. | |
| 5,378,475 A | 1/1995 | Smith et al. | |
| 5,410,016 A | 4/1995 | Hubbell et al. | |
| 5,443,505 A | 8/1995 | Wong et al. | |
| 5,518,730 A | 5/1996 | Fuisz | |
| 5,518,731 A | 5/1996 | Meadows | |
| 5,587,175 A | 12/1996 | Viegas et al. | |
| 5,620,699 A | 4/1997 | Meadows | |
| 5,626,863 A | 5/1997 | Hubbell et al. | |
| 5,660,851 A | 8/1997 | Domb | |
| 5,731,005 A | 3/1998 | Ottoboni et al. | |
| 5,766,242 A | 6/1998 | Wong et al. | |
| 5,807,581 A | 9/1998 | Rosenblatt et al. | |
| 5,824,072 A | 10/1998 | Wong | |
| 5,869,079 A | 2/1999 | Wong et al. | |
| 5,958,443 A | 9/1999 | Viegas et al. | |
| 6,004,573 A | 12/1999 | Rathi et al. | |
| 6,022,554 A | 2/2000 | Lee et al. | |
| 6,060,582 A | 5/2000 | Hubbell et al. | |
| 6,063,116 A | 5/2000 | Kelleher | |
| 6,063,396 A | 5/2000 | Kelleher | |
| 6,074,661 A | 6/2000 | Olejnik et al. | |
| 6,117,949 A | 9/2000 | Rathi et al. | |
| 6,217,895 B1 | 4/2001 | Guo et al. | |

(Continued)

FOREIGN PATENT DOCUMENTS

| | | |
|---|---|---|
| EP | 0311065 A1 | 4/1989 |
| JP | S62-201816 A | 5/1987 |

(Continued)

OTHER PUBLICATIONS

Ram et al.; "Phacoemulsification and intraocular lens implantation after inadvertent intracapsular injection of intravitreal dexamethasone implant"; BMJ Case Reports; (2012); pp. 1-3; vol. 2012; BMJ Publishing Group.doi:10.1136/bcr2012007494.

(Continued)

Primary Examiner — Edelmira Bosques
(74) Attorney, Agent, or Firm — Thorpe North & Western, LLP

(57) ABSTRACT

An intraocular active agent delivery device can include an active agent homogenously combined with a biodegradable active agent matrix such that the entire delivery device is homogenous. The homogenous delivery device can have a shape and size to fit within a lens capsule or ciliary sulcus of an eye and provide a therapeutically effective amount of the active agent to the eye. The biodegradable active agent matrix can be formulated to provide sustained release of the therapeutically effective amount of the active agent during a release period. In some examples, the active agent can include dexamethasone.

23 Claims, 13 Drawing Sheets

(56) References Cited

U.S. PATENT DOCUMENTS

| | | |
|---|---|---|
| 6,217,896 B1 | 4/2001 | Benjamin |
| 6,264,971 B1 | 7/2001 | Darougar et al. |
| 6,309,669 B1 | 10/2001 | Setterstrom et al. |
| 6,331,313 B1 | 12/2001 | Wong et al. |
| 6,369,112 B1 | 4/2002 | Xia |
| 6,369,116 B1 | 4/2002 | Wong et al. |
| 6,416,777 B1 | 7/2002 | Yaacobi |
| 6,548,078 B2 | 4/2003 | Guo et al. |
| 6,627,600 B2 | 9/2003 | Boutignon |
| 6,699,493 B2 | 3/2004 | Wong |
| 6,713,081 B2 | 3/2004 | Robinson et al. |
| 6,726,918 B1 | 4/2004 | Wong et al. |
| 6,726,920 B1 | 4/2004 | Theeuwes et al. |
| 6,756,049 B2 | 6/2004 | Brubaker et al. |
| 7,033,605 B2 | 4/2006 | Wong |
| 7,048,946 B1 | 5/2006 | Wong et al. |
| 7,083,802 B2 | 8/2006 | Peyman |
| 7,090,888 B2 | 8/2006 | Snyder et al. |
| 7,186,789 B2 | 3/2007 | Hossainy et al. |
| 7,195,774 B2 | 3/2007 | Carvalho et al. |
| 7,455,855 B2 | 11/2008 | Kuwano et al. |
| 7,527,621 B2 | 5/2009 | Greenberg |
| 7,544,371 B2 | 6/2009 | Kunzler et al. |
| 7,585,517 B2 | 9/2009 | Cooper et al. |
| 7,589,057 B2 | 9/2009 | Chang et al. |
| 7,625,582 B2 | 12/2009 | Wong |
| 7,658,364 B2 | 2/2010 | Robinson et al. |
| 7,749,530 B2 | 7/2010 | Spada et al. |
| 7,767,223 B2 | 8/2010 | Wong |
| 7,771,742 B2 | 8/2010 | Hughes et al. |
| 7,799,336 B2 | 9/2010 | Hughes |
| 7,846,468 B2 | 12/2010 | Wong |
| 7,847,025 B2 | 12/2010 | Liu et al. |
| 8,231,892 B2 | 7/2012 | Lyons et al. |
| 8,802,129 B2 | 8/2014 | Whitcup et al. |
| 9,012,437 B2 | 4/2015 | Wong et al. |
| 2002/0039594 A1 | 4/2002 | Unger |
| 2004/0126408 A1 | 7/2004 | Kabra et al. |
| 2004/0137059 A1 | 7/2004 | Nivaggioli et al. |
| 2004/0208909 A1 | 10/2004 | Brubaker et al. |
| 2004/0253293 A1 | 12/2004 | Shafiee et al. |
| 2005/0031669 A1 | 2/2005 | Shafiee et al. |
| 2005/0048098 A1 | 3/2005 | Wong et al. |
| 2005/0048099 A1 | 3/2005 | Shiah et al. |
| 2005/0244458 A1* | 11/2005 | Huang ............... A61K 31/5377 424/426 |
| 2005/0244461 A1 | 11/2005 | Nivaggioli et al. |
| 2005/0244462 A1 | 11/2005 | Farooq |
| 2005/0244463 A1 | 11/2005 | Huang et al. |
| 2005/0244465 A1 | 11/2005 | Nivaggioli et al. |
| 2005/0244467 A1 | 11/2005 | Nivaggioli et al. |
| 2005/0244468 A1 | 11/2005 | Huang et al. |
| 2005/0244469 A1 | 11/2005 | Whitcup et al. |
| 2005/0244471 A1 | 11/2005 | Shiah et al. |
| 2005/0244472 A1 | 11/2005 | Hughes et al. |
| 2005/0244473 A1 | 11/2005 | Hughes et al. |
| 2005/0244474 A1 | 11/2005 | Huang et al. |
| 2005/0244476 A1 | 11/2005 | Burke et al. |
| 2005/0244478 A1 | 11/2005 | Hughes et al. |
| 2005/0244479 A1 | 11/2005 | Huang et al. |
| 2005/0255144 A1 | 11/2005 | Schultz |
| 2005/0271705 A1 | 12/2005 | Hughes et al. |
| 2005/0281861 A1 | 12/2005 | Hughes et al. |
| 2006/0008506 A1 | 1/2006 | Cipriano De Sousa et al. |
| 2006/0067978 A1 | 3/2006 | Heiler et al. |
| 2006/0078592 A1 | 4/2006 | Kunzler et al. |
| 2006/0110429 A1 | 5/2006 | Reiff et al. |
| 2006/0134174 A1 | 6/2006 | Bartels et al. |
| 2006/0134175 A1 | 6/2006 | Bartels |
| 2006/0134176 A1 | 6/2006 | Bartels |
| 2006/0182781 A1 | 8/2006 | Hughes et al. |
| 2006/0182783 A1 | 8/2006 | Hughes et al. |
| 2006/0198871 A1 | 9/2006 | Wong |
| 2006/0216328 A1 | 9/2006 | Kis et al. |
| 2006/0233859 A1 | 10/2006 | Whitcup et al. |
| 2006/0233860 A1 | 10/2006 | Chang et al. |
| 2006/0257450 A1 | 11/2006 | Mudumba et al. |
| 2006/0257452 A1 | 11/2006 | Hughes et al. |
| 2006/0263409 A1 | 11/2006 | Peyman |
| 2006/0292202 A1 | 12/2006 | Bartels |
| 2006/0292203 A1 | 12/2006 | Dellamary et al. |
| 2007/0059336 A1 | 3/2007 | Hughes et al. |
| 2007/0178138 A1 | 8/2007 | Pal et al. |
| 2007/0212395 A1 | 9/2007 | Donello et al. |
| 2007/0212397 A1 | 9/2007 | Roth |
| 2007/0224247 A1 | 9/2007 | Chudzik et al. |
| 2007/0280995 A1 | 12/2007 | Rabinovich-Guilatt et al. |
| 2007/0281914 A1 | 12/2007 | Rabinovich-Guilatt et al. |
| 2007/0298073 A1 | 12/2007 | Whitcup et al. |
| 2007/0298074 A1 | 12/2007 | Robinson et al. |
| 2007/0298076 A1 | 12/2007 | Wong |
| 2008/0038316 A1 | 2/2008 | Wong et al. |
| 2008/0038317 A1 | 2/2008 | Chang et al. |
| 2008/0050420 A1 | 2/2008 | Wong |
| 2008/0050421 A1 | 2/2008 | Wong |
| 2008/0057101 A1 | 3/2008 | Roorda |
| 2008/0057102 A1 | 3/2008 | Roorda |
| 2008/0057103 A1 | 3/2008 | Roorda |
| 2008/0063687 A1 | 3/2008 | Chou et al. |
| 2008/0069859 A1 | 3/2008 | Wong |
| 2008/0107712 A1 | 5/2008 | Shiah et al. |
| 2008/0124376 A1 | 5/2008 | Pruitt et al. |
| 2008/0145403 A1 | 6/2008 | Spada et al. |
| 2008/0145405 A1 | 6/2008 | Kunzler et al. |
| 2008/0145406 A1 | 6/2008 | Asgharian |
| 2008/0147021 A1 | 6/2008 | Jani |
| 2008/0152694 A1 | 6/2008 | Lobl et al. |
| 2008/0131481 A1 | 7/2008 | Hughes |
| 2008/0131484 A1 | 7/2008 | Robinson et al. |
| 2008/0167600 A1 | 7/2008 | Peyman |
| 2008/0172014 A1 | 7/2008 | Whitcup et al. |
| 2008/0181929 A1 | 7/2008 | Robinson et al. |
| 2008/0200860 A1 | 8/2008 | Tu et al. |
| 2008/0233171 A1 | 9/2008 | Whitcup et al. |
| 2008/0233172 A1 | 9/2008 | Whitcup et al. |
| 2008/0233173 A1 | 9/2008 | Whitcup et al. |
| 2008/0241219 A1 | 10/2008 | Whitcup et al. |
| 2008/0241220 A1 | 10/2008 | Whitcup et al. |
| 2008/0241221 A1 | 10/2008 | Whitcup et al. |
| 2008/0241222 A1 | 10/2008 | Whitcup et al. |
| 2008/0241223 A1 | 10/2008 | Nivaggioli et al. |
| 2008/0268021 A1 | 10/2008 | Warren et al. |
| 2008/0269119 A1 | 10/2008 | Griffith et al. |
| 2008/0286334 A1 | 11/2008 | Shiah et al. |
| 2008/0286336 A1 | 11/2008 | Shiah et al. |
| 2008/0292679 A1 | 11/2008 | Lyons et al. |
| 2009/0093780 A1 | 4/2009 | Tuitupou et al. |
| 2009/0130176 A1 | 5/2009 | Bossy-Nobs et al. |
| 2009/0148498 A1 | 6/2009 | Libin et al. |
| 2009/0162417 A1 | 6/2009 | Eells |
| 2009/0196905 A1 | 8/2009 | Spada et al. |
| 2009/0196906 A1 | 8/2009 | Spada et al. |
| 2009/0214619 A1 | 8/2009 | Reiff et al. |
| 2009/0220572 A1 | 9/2009 | Deschatelets et al. |
| 2009/0258924 A1 | 10/2009 | Lyons et al. |
| 2009/0274744 A1 | 11/2009 | Kunzler et al. |
| 2009/0274745 A1 | 11/2009 | Kunzler et al. |
| 2009/0286773 A1 | 11/2009 | Spada et al. |
| 2009/0324687 A1 | 12/2009 | Cooper et al. |
| 2009/0324688 A1 | 12/2009 | Cooper et al. |
| 2009/0324689 A1 | 12/2009 | Cooper et al. |
| 2009/0324690 A1 | 12/2009 | Cooper et al. |
| 2010/0119519 A1 | 5/2010 | Peyman |
| 2010/0158980 A1 | 6/2010 | Kopezynski et al. |
| 2010/0189766 A1 | 7/2010 | Utkhede et al. |
| 2010/0209478 A1 | 8/2010 | Sawhney et al. |
| 2010/0215720 A1 | 8/2010 | Garagorri Ganchegui et al. |
| 2010/0247606 A1 | 9/2010 | Robinson et al. |
| 2010/0255061 A1 | 10/2010 | De Juan, Jr. et al. |
| 2010/0311808 A1 | 12/2010 | Lyons et al. |
| 2011/0125090 A1 | 5/2011 | Peyman |

(56) References Cited

U.S. PATENT DOCUMENTS

2011/0230963 A1  9/2011 Cuevas
2013/0218081 A1  8/2013 Roth

FOREIGN PATENT DOCUMENTS

| JP | H11506450 A | 6/1999 |
|----|----|----|
| JP | 2004210798 A | 7/2004 |
| JP | 2007217699 A | 8/2007 |
| JP | 2007535535 A | 12/2007 |
| JP | 2008523131 A | 7/2008 |
| JP | 2009508646 A | 3/2009 |
| WO | WO 2007/035473 | 3/2007 |
| WO | WO 2008/025111 A2 | 3/2008 |
| WO | WO 2009/140246 | 11/2009 |

OTHER PUBLICATIONS

Vianna et al.; "Intracapsular dexamethasone implant in patients undergoing phacoemulsification and intraocular lens implantation"; Arq. Bras. Oftalmol.; (Jul.-Aug. 2013); pp. 226-228; vol. 76, No. 4.

* cited by examiner

INTRAOCULAR DRUG DELIVERY DEVICE AND ASSOCIATED METHODS

RELATED APPLICATIONS

This application is a continuation-in-part of U.S. application Ser. No. 15/391,666, filed Dec. 27, 2016, which is a continuation-in-part of U.S. application Ser. No. 13/543,597, filed Jul. 6, 2012, which is a continuation-in-part of U.S. application Ser. No. 13/211,169, filed Aug. 16, 2011 and now issued as U.S. Pat. No. 9,095,404, which is a continuation-in-part of U.S. application Ser. No. 12/945,428, filed Nov. 12, 2010 and now issued as U.S. Pat. No. 8,663,194, which is a continuation-in-part of International Application No. PCT/US2009/043566, filed May 12, 2009, which claims priority to U.S. Provisional Application No. 61/052,507, filed May 12, 2008, which are each incorporated herein by reference.

FIELD OF THE INVENTION

The present invention relates to systems, methods, and devices for the sustained and targeted (local) delivery of a pharmaceutical active agent into a subject's eye. Accordingly, the present invention involves the fields of polymer chemistry, material science, polymer science, drug delivery, formulation science, pharmaceutical sciences, and medicine, particularly ophthalmology.

BACKGROUND

Age-related macular degeneration (AMD) and glaucoma are two of the leading causes of blindness in the United States and across the world. Present glaucoma therapies generally require polypharmacy, where subjects are often prescribed several topical agents that must be applied to the eye with varying frequencies, in some cases up to 3 or 4 times a day. These dosing regimens are often difficult for subjects to consistently follow, and many individuals progress to needing surgical treatments such as intraocular shunts or trabeculectomies, which have significant attendant complications.

Subjects having macular degeneration are often required to have monthly intravitreal injections. Such injections are painful and may lead to retinal detachment, endophthalmitis, and other complications. Furthermore, these injections are generally performed only by retinal surgeons, a small fraction of the ophthalmic community, producing a bottleneck in eye care delivery and increased expense.

Postoperative surgery inflammation is associated with raise intraocular pressure (TOP), and increase the likelihood of cystoid macular edema (CME), synechial formation, posterior capsule opacification (PCO), and secondary glaucoma. Patient compliance is of concern in the management of postoperative inflammation because multiple eye drops must be taken multiple times per day at regular intervals over the course of weeks. Poor compliance compromises the efficacy of topical drugs, which are further limited by corneal absorption and have highly variable intraocular concentrations during the therapeutic course. Uveitis specifically refers to inflammation of the middle layer of the eye, termed the "uvea" but in common usage may refer to any inflammatory process involving the interior of the eye. Uveitis is estimated to be responsible for approximately 10% of the blindness in the United States.

Postoperative cataract surgery inflammation can be well controlled by improving patient compliance. Available literature and experience shows penetration of the drug after topical administration is poor and higher systemic concentration means frequent systemic adverse events. All of these factors highlight the need for sustained intraocular delivery for pharmaceutical active agents to effectively control inflammation.

SUMMARY

An intraocular active agent delivery device can include an active agent homogenously combined with a biodegradable active agent matrix such that the entire delivery device is homogenous. The homogenous delivery device can have a shape and size to fit within a lens capsule or ciliary sulcus of an eye and provide a therapeutically effective amount of the active agent to the eye. The biodegradable active agent matrix can be formulated to provide sustained release of the therapeutically effective amount of the active agent during a release period. In some examples, the active agent can include dexamethasone.

A method of treating an eye condition can include inserting an intraocular active agent delivery device into the lens capsule or ciliary sulcus of an eye. The intraocular active agent delivery device can include an active agent homogenously combined with a biodegradable active agent matrix such that the entire delivery device is homogenous. The homogenous delivery device can have a shape and size to provide a therapeutically effective amount of the active agent to the eye. The biodegradable active agent matrix can be formulated to provide sustained release of the therapeutically effective amount of the active agent during a release period. In some examples, the active agent can include dexamethasone. The method can further include allowing the biodegradable active agent matrix to biodegrade to provide sustained release of the therapeutically effective amount of the active agent to the eye during the release period.

There has thus been outlined, rather broadly, the more important features of the invention so that the detailed description thereof that follows may be better understood, and so that the present contribution to the art may be better appreciated. Other features of the present invention will become clearer from the following detailed description of the invention, taken with the accompanying drawings and claims, or may be learned by the practice of the invention.

DETAILED DESCRIPTION OF THE INVENTION

Figure 1:
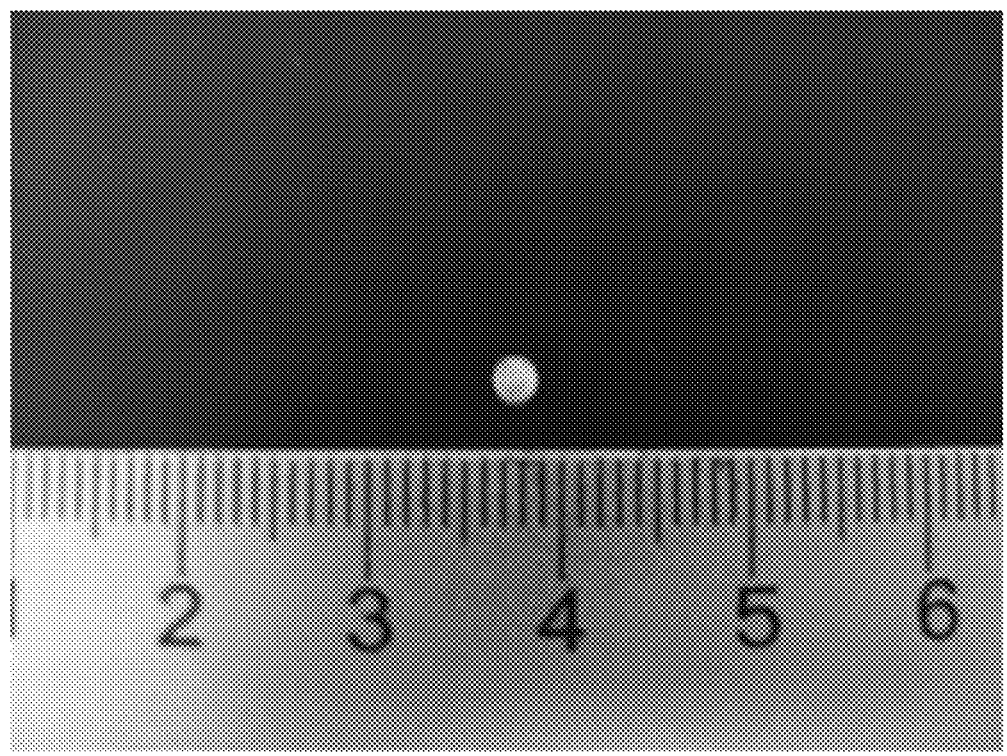
FIG. 1 is a photograph showing a bioerodible dexamethasone implant (BDI), in accordance with some examples of the present disclosure.
Figure 2:
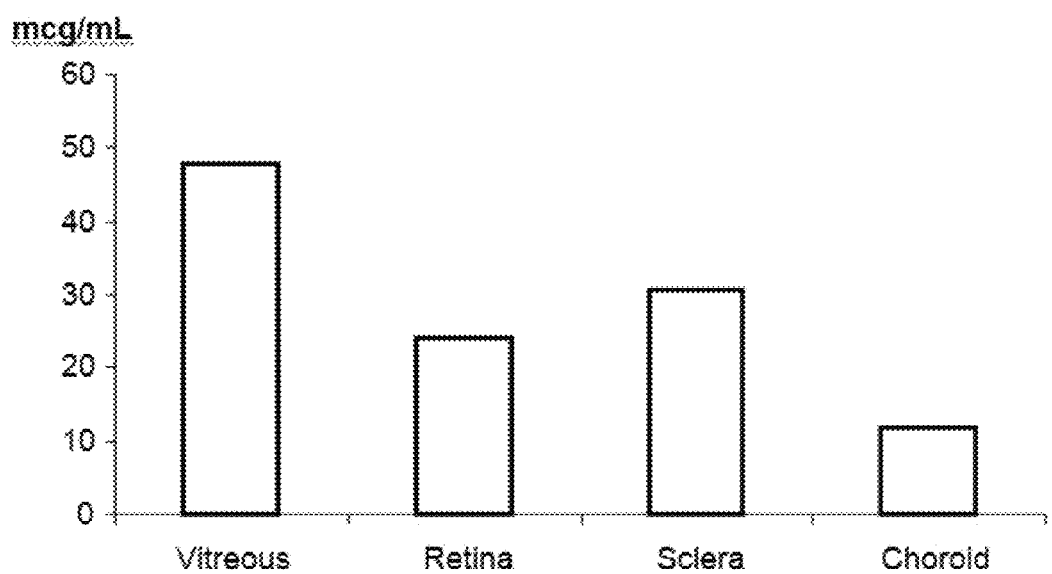
FIG. 2 is a bar graph showing the amount of an active agent present in various eye tissues following implantation of an intraocular device in accordance with a further aspect of the present invention.
Figure 3:
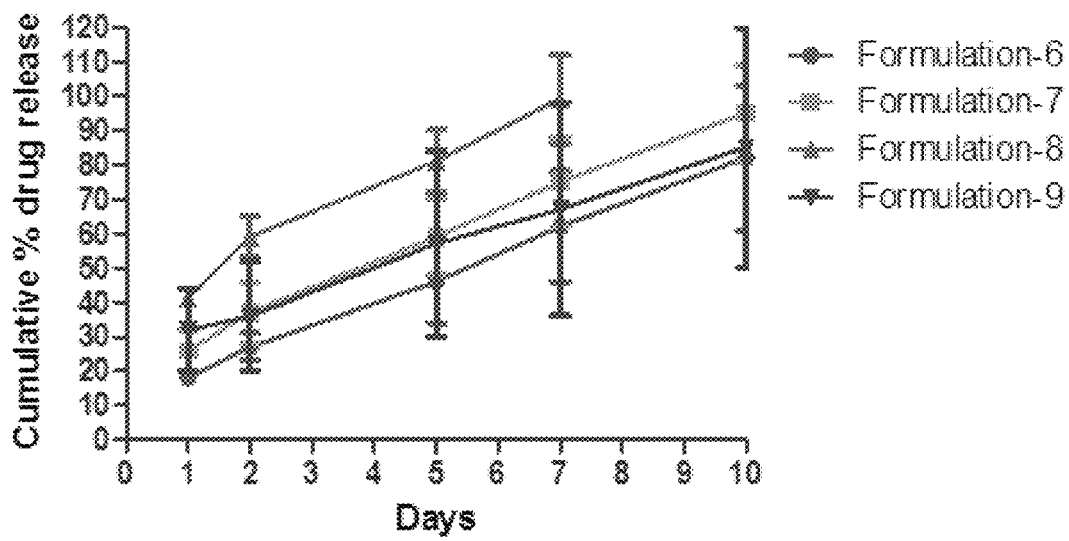
FIG. 3 is a graph of in-vitro release kinetics of an example BDI implant. Data are presented as mean±SD (n=3).
Figure 4:
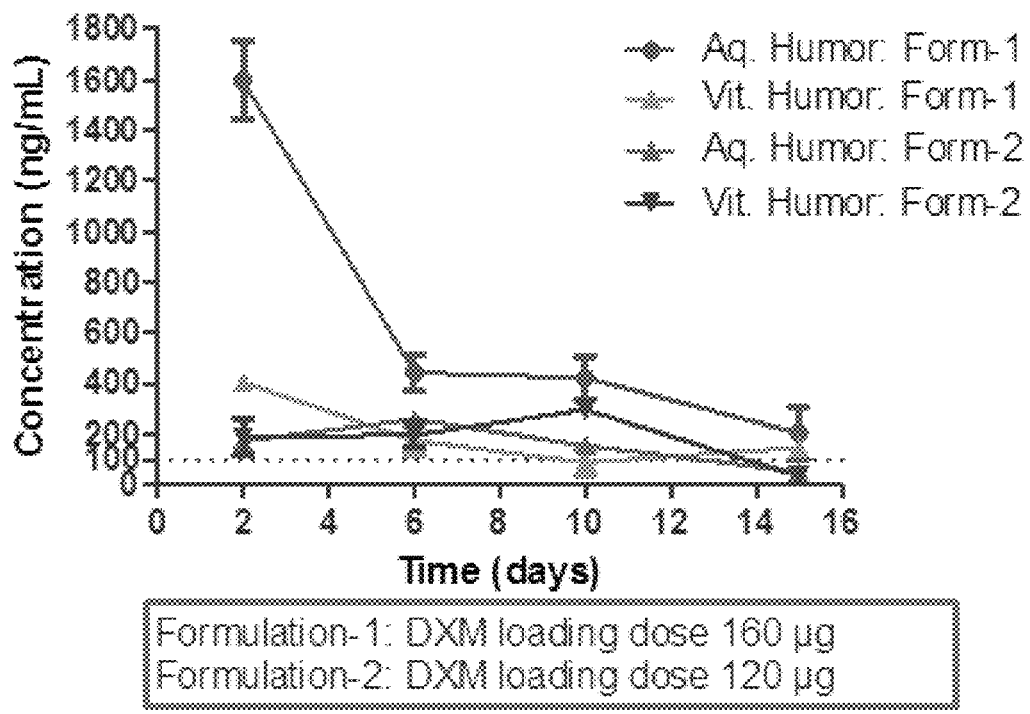
FIG. 4 time vs concentration profile of an example BDI implant with 120 to 160 µg of dexamethasone (DXM) in aqueous and vitreous humor of New Zealand White (NZW) rabbits.

The following detailed description of exemplary embodiments of the invention makes reference to the accompanying drawings, which form a part hereof and in which are shown, by way of illustration, exemplary embodiments in which the invention may be practiced. While these exemplary embodiments are described in sufficient detail to enable those skilled in the art to practice the invention, it should be understood that other embodiments may be realized and that various changes to the invention may be made without departing from the spirit and scope of the present invention. Thus, the following more detailed description of the embodiments of the present invention is not intended to limit the scope of the invention, as claimed, but is presented for purposes of illustration only and not limitation to describe the features and characteristics of the present invention, to set forth the best mode of operation of the invention, and to sufficiently enable one skilled in the art to practice the invention. Accordingly, the scope of the present invention is to be defined solely by the appended claims.

It must be noted that, as used in this specification and the appended claims, the singular forms "a," "an," and "the" include plural referents unless the context clearly dictates otherwise. Thus, for example, reference to "a drug" includes reference to one or more of such drugs, "an excipient" includes reference to one or more of such excipients, and "filling" refers to one or more of such steps.

Definitions

In describing and claiming the present invention, the following terminology will be used in accordance with the definitions set forth below.

As used herein, "active agent," "bioactive agent," "pharmaceutically active agent," and "drug," may be used interchangeably to refer to an agent or substance that has measurable specified or selected physiologic activity when administered to a subject in a significant or effective amount. These terms of art are well-known in the pharmaceutical and medicinal arts.

As used herein, "formulation" and "composition" may be used interchangeably herein, and refer to a combination of two or more elements, or substances. In some embodiments a composition can include an active agent, an excipient, or a carrier to enhance delivery, depot formation, etc.

As used herein, "effective amount" refers to an amount of an ingredient which, when included in a composition, is sufficient to achieve an intended compositional or physiological effect. Thus, a "therapeutically effective amount" refers to a substantially non-toxic, but sufficient amount of an active agent, to achieve therapeutic results in treating or preventing a condition for which the active agent is known to be effective. It is understood that various biological factors may affect the ability of a substance to perform its intended task. Therefore, an "effective amount" or a "therapeutically effective amount" may be dependent in some instances on such biological factors. Further, while the achievement of therapeutic effects may be measured by a physician or other qualified medical personnel using evaluations known in the art, it is recognized that individual variation and response to treatments may make the achievement of therapeutic effects a subjective decision. However, the determination of an effective amount is well within the ordinary skill in the art of pharmaceutical and nutritional sciences as well as medicine.

As used herein, "subject" refers to a mammal that may benefit from the administration of a composition or method as recited herein. Examples of subjects include humans, and can also include other animals such as horses, pigs, cattle, dogs, cats, rabbits, aquatic mammals, etc.

As used herein, the term "intraocular lens" refers to a lens that is utilized to replace a lens in the eye of a subject. Such intraocular lenses can be synthetic or biological in nature. Furthermore, in some aspects the term "intraocular lens" can also refer to the original natural lens that is associated with the eye.

As used herein, the term "ciliary sulcus" refers to the space between the posterior root of the iris and the ciliary body of the eye.

As used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result. For example, a composition that is "substantially free of" particles would either completely lack particles, or so nearly completely lack particles that the relevant effect would be the same as if it completely lacked particles. In other words, a composition that is "substantially free of" an ingredient or element may still actually contain such item as long as there is no measurable effect thereof.

As used herein, the term "about" is used to provide flexibility to a numerical range endpoint by providing that a given value may be "a little above" or "a little below" the endpoint.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

As used herein, the term "at least one of" is intended to be synonymous with "one or more of." For example, "at least one of A, B and C" explicitly includes only A, only B, only C, and combinations of each.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc. This same principle applies to ranges reciting only one numerical value. Furthermore, such an interpretation should apply regardless of the breadth of the range or the characteristics being described.

Any steps recited in any method or process claims may be executed in any order and are not limited to the order presented in the claims unless otherwise stated. Means-plus-function or step-plus-function limitations will only be employed where for a specific claim limitation all of the following conditions are present in that limitation: a) "means for" or "step for" is expressly recited; and b) a corresponding function is expressly recited. The structure, material or acts that support the means-plus function are expressly recited in the description herein. Accordingly, the scope of the invention should be determined solely by the appended claims and their legal equivalents, rather than by the descriptions and examples given herein.

Intraocular Drug Delivery Device

An intraocular drug delivery device can provide improved ophthalmic drug delivery by alleviating the need for multiple injections or complex eyedrop regimens by providing an intra-capsular homogeneous matrix reservoir which is implantable and biodegrades such that subsequent surgery is often unnecessary. Further, the device can deliver a variety or combination of different medicines.

A novel intraocular drug delivery device, system, and associated methods for providing sustained release of ocular active agents for extended periods of time are disclosed and described. One problem with many eye diseases, such as Age-related Macular Degeneration (AMD), is the constant need for a subject to receive painful ocular injections, which have significant risks of retinal detachment, vitreous hemorrhage, and endophthalmitis. The intraocular drug delivery device allows for sustained release of an active agent over time, thus eliminating the need for frequent ocular injections.

It should be noted that neovascularization is a key pathobiological process in a variety of eye diseases, such as AMD, proliferative diabetic retinopathy, vascular occlusive disease, and radiation retinopathy. Additionally, the incidence of glaucoma is increasing worldwide. Many other disorders, including severe uveitis and geographic atrophy in AMD, can be treated using such an intraocular drug delivery device. Thus, an implantable, generally sutureless drug delivery device for placement in the anterior segment of the eye has great potential to improve the quality of life for subjects.

The drug delivery device can continuously deliver dexamethasone or other anti-inflammatory or therapeutic agents with near zero order kinetics for two weeks or more. Treatment of uveitis needs long term (6-8 weeks) sustained delivery of anti-inflammatory agents. The biggest disadvantage with topical drops is that negligible concentrations of drugs will reach the posterior segment of the eye and especially the retina/choroid. The designed and disclosed drug delivery device can deliver dexamethasone and/or other therapeutic agents continuously with near zero order kinetics both to the anterior and posterior segments of the eye, thus effectively controlling the inflammation.

It some instances it is desirable to have a burst effect of drug over the 24 or 48 hours followed by a near zero order delivery kinetics subsequent to the initial 24 to 48 hours. In some cases, the burst can deliver up to 10, 20, or up to 30% with in the first day or two while in other cases it can be desirable to have no burst effect where less than 5% of the drug is delivered in the first day or two. In the case of steroid delivery a burst effect may be advantageous to more closely mimic the dosing regimens. The use of croscarmellose and other disintegrants and/or super-disintegrants controls how much drug is released in the first day or two. As a general guideline, an amount of disintegrant can range from 0 to 20 wt % of the matrix. Furthermore, annealing conditions during manufacturing and storage conditions after manufacturing can also aid in controlling the burst affect. For example, storage and implant temperature maintained near ambient temperature can increase initial burst delivery, while cooler temperatures such as 2 to 8° C. can decrease initial burst delivery. Similarly, annealing of the device can decrease the burst effect. For example, annealing at an anneal temperature from 50 to 90° C. (and in some cases 60 to 80° C.) for 15 to 45 minutes can markedly reduce burst effect. Thus, the burst effect can be varied or eliminated based on a desired therapeutic effect and delivery profile.

Therefore, the opportunity exists to improve management of AMD, postoperative surgery inflammation, and uveitis patients undergoing cataract surgery by sustained release of pharmaceutical active agent(s). Accordingly, the present invention provides systems, devices, and associated methods for the delivery of active agents into the eye of a subject. In some examples, the systems, devices, and associated methods can be positioned within the anterior segment of the eye (e.g. within the lens capsule) of a subject to deliver an active agent to the posterior segment of an eye of the subject. Non-limiting examples of ocular regions found within the posterior segment of the eye can include at least one of the vitreous humor, the choroid, and the retina. In addition to delivering the active agent to the posterior segment of the eye, the active agent can also be delivered to the anterior segment of the eye. The anterior segment of the eye can include at least one of the aqueous humor, the iris, and the lens capsule. In one aspect, the intraocular device can be sutureless. A sutureless device can be defined as a device or structure that can be inserted and retained within a lens capsule without the need for a suture to hold the device in place.

In further detail, in some aspects, the device can be implantable within the lens capsule (e.g. after removal of a native lens) during cataract surgery, essentially "piggybacking" on the cataract extraction, and thus eliminating the need for additional surgical procedures. One benefit to "piggybacking" on the cataract extraction is the ability to deliver steroids, antibiotics, and/or various non-steroidal agents directly to the eye after surgery, thus helping to minimize complications such as cystoid macular edema.

In other aspects, the device can be implanted in a surgery that is separate from a cataract procedure, e.g., subsequent to a previous cataract extraction with reopening of the lens capsule. For example, the device can be implanted post-cataract surgery for treatment of macular degeneration, retinal vein or artery occlusion, diabetic retinopathy, macular edema (e.g. from diabetes, uveitis, intraocular surgery, etc.), retinal degenerations where a neuroprotectant delivery is indicated, or the like.

In one embodiment, the device can be provided in the form of an implant containing an active agent within a biodegradable or bioerodible polymer matrix. The biodegradable active agent matrix can include an active agent in an amount to deliver a therapeutically effective amount or therapeutically effective dose of the active agent to the posterior segment of the eye from the lens capsule. A therapeutically effective amount or therapeutically effective dose can vary depending on the particular therapeutic agent being employed in the biodegradable active agent matrix. Further, the therapeutically effective amount or therapeutically effective dose can vary depending on the severity of the condition being treated. Nonetheless, the active agent can be present in an amount to facilitate delivery of the active agent from the anterior segment of the eye (e.g. from the lens capsule) to the posterior segment of the eye.

The therapeutically effective amount or therapeutically effective dose can typically range from about 50 micrograms (mcg) to about 10 milligrams (mg), depending on the active agent being employed and the severity of the condition. In some specific examples, the therapeutically effective amount or therapeutically effective dose can range from about 50 mcg to about 600 mcg. In yet other examples, the therapeutically effective amount or therapeutically effective dose can range from about 100 mcg to about 400 mcg, from about 100 mcg to about 300 mcg, or from about 200 mcg to about 400 mcg. In yet further detail, the active agent can typically be present in the implant at a concentration of from about 5 wt % to about 25 wt %, or from about 5 wt % to about 15 wt %, or from about 10 wt % to about 20 wt %, although up to about 50 wt % can be useful in some applications. Further still, depending on the dosage requirements, one, two or more implants can be implanted per eye to achieve a therapeutically effective dose.

The biodegradable active agent matrix can be configured to bioerode to provide controlled release of the therapeutically effective amount over a period of days, weeks, or months. In some examples, the therapeutically effective amount can be released over a period ranging from about 1 week to about 10 weeks. In other examples, the therapeutically effective amount can be released over a period ranging from about 1 week to about 3 weeks, from about 2 weeks to about 6 weeks, or from about 5 weeks to about 8 weeks. In cases such as retinal vein/artery occlusion, diabetic retinopathy, macular edema or retinal degenerations, the period can often range from 2 months to 12 months, and in some cases from 2.5 months to 5 months. For example, bioerodible lipid polymers and/or bioerodible polycaprolactone can be used as an extended release matrix material.

Thus, in some examples, the delivery device can release from about 50 mcg to about 10 mg of active agent over a period of from about 1 week to about 12 months. In some additional examples, the delivery device can release from about 50 mcg to about 600 mcg of active agent over a period of from about 1 week to about 10 weeks. In yet other examples, the delivery device can release from about 100 mcg to about 400 mcg of active agent over a period of from about 2 weeks to about 8 weeks. In still other examples, the delivery device can release from about 100 mcg to about 300 mcg, or from about 200 mcg to about 400 mcg of active agent over a period of from about 2 weeks to about 8 weeks. In two specific examples, the delivery device can release 200 mcg over 2-3 weeks or 300 mcg over 6-8 weeks.

In some specific examples, the delivery device can deliver an average of from about 0.5 mcg to about 90 mcg per day of the active agent during a release period, and in some cases up to about 30 mcg per day. In other examples, the delivery device can deliver an average of from about 1 mcg to about 12 mcg per day of the active agent during a release period. In yet other examples, the delivery device can deliver an average of from about 2 mcg to about 8 mcg per day of the active agent during a release period.

It is noted that in addition to the amount of the active agent present in the biodegradable active agent matrix, other additional factors can affect the delivery of the active agent to the posterior segment of the eye. For example, the intracapsular positioning of the device within the lens capsule can affect delivery of the active agent to the posterior segment of the eye. In some examples, positioning of the implant at a location inferior and peripheral to the intraocular lens (IOL) or within the inferior peripheral capsule can provide suitable delivery of the active agent to the posterior segment of the eye. Typically, the implant can also be located at a lower portion within the lens capsule. For example, the implant can be oriented within the inferior periphery, annular periphery encircling the intraocular lens for at least 180 degrees, or the like as long as a line of sight is not obstructed.

Further still, the molecular weight and molecular size of the active agent can affect delivery of the active agent to the posterior segment of the eye. Thus, in some examples, the active agent can have a molecular weight of 250,000 daltons (Da) or less. In yet other examples, the active agent can have a molecular weight of 170,000 Da or less. In yet additional examples, the active agent can have a molecular weight of 500 Da or less.

Numerous active agents are known for the treatment or prophylaxis of various eye conditions, such as AMD (neovascular form or atrophic form), glaucoma, diabetic retinopathy, Retinopathy of Prematurity, uveitis, corneal transplant rejection, capsular fibrosis, posterior capsule opacification, retinal vein occlusions, infections, and the like. Any suitable active agent for incorporation into a biodegradable active agent matrix can be used, such as steroids, NSAIDs, antibiotics, anti-VEGF agents, PDGF-B inhibitors (FOVISTA®), integrin antagonists, complement antagonists, the like, or combinations thereof. Non-limiting examples of suitable active agents can include dexamethasone, prednisolone, bevacizumab (AVASTIN®), ranibizumab (LUCENTIS®), sunitinib, pegaptanib (MACUGEN®), moxifloxacin, gatifloxacin, besifloxacin, timolol, latanoprost, brimonidine, nepafenac, bromfenac, diclofenac, ketorolac, triamcinolone, difluprednate, fluocinolide, aflibercept, the like, or combinations thereof. Treatment regimens can additionally include various photodynamic therapies, and the like. In one specific example, the active agent can include dexamethasone.

The bioerodible polymer matrix can include one or several excipients, which can depend on the duration of active agent delivery. Non-limiting examples of active agent matrix materials can include polymeric and non-polymeric materials. Specific non-limiting examples of suitable matrix materials include biodegradable polymers such as PLGA (different ratios of lactic to glycolide content and end groups such as acid or ester termination), PVA, PEG, PLA, PGA, hydroxypropylcellulose, sodium carboxymethylcellulose, croscarmellose sodium, polycaprolactone, hyaluronic acid, albumin, sodium chloride block copolymers thereof, and the like. Specific copolymers such as polylactic-polyglycolic acid block copolymers (PLGA), polyglycolic acid-polyvinyl alcohol block copolymers (PGA/PVA), hydroxypropylmethylcellulose (HPMC), polycaprolactone-polyethylene glycol block copolymers, croscarmellose, and the like can be particularly effective. In one aspect, the active agent matrix can be a PLGA having about 45-80% PLA and 55-20% PGA such as about 65% PLA and 35% PGA, and in one case about 50% PLA and 50% PGA. In another alternative embodiment, the weight ratios of PLGA, dexamethasone, and Croscarmellose sodium can be 60-90/5-25/5-25 or 50-75/10-40/10-40 ratios. In another aspect, the biodegradable active agent matrix comprises a low melt fatty acid such as, but not limited to, lauric acid, myrisitic acid, palmitic acid, stearic acid, arachidic acid, capric acid, oleic acid, palmitoleic acid, and mixtures thereof. In one aspect, the biodegradable active agent matrix can comprise a pharmaceutically acceptable disintegrant. In one example, the disintegrant can be a superdistintegrant. Non-limiting examples of suitable disintigrants include crosslinked celluloses (e.g. croscarmellose, AC-DI-SOL®, NYMCEL® ZSX, PRIMELLOSE®, SOLUTAB®, VIVASOL®), microcrystalline cellulose, alginates, crosslinked PVP (e.g. crospovidone, KOLLIDON®, POLYPLASDONE™), crosslinked starch, soy polysaccharides, calcium silicate, salts thereof, and the like. In one example, a disintigrant can include croscarmellose from 3 wt % to 25 wt %, and in one case from 3 wt % to 20 wt % of the active agent matrix. Croscarmellose at greater than about 25 wt % can be useful for delivery times less than about 1 week, while less than about 3% can be useful for extended delivery times of greater than 6 to 9 months.

Typically, the delivery device herein can be targeted for a relatively short delivery duration, such as less than eight weeks. In some examples, the active agent has a delivery duration of from about two weeks to about six or eight weeks. Delivery duration can be a function of the type of polymer used in the matrix, copolymer ratios, and other factors. Although other biodegradable polymers can be suitable such as those listed previously, particularly suitable polymers can include at least one of poly(lactic-co-glycolide), hydroxypropyl methyl cellulose, hydroxyl methyl cellulose, polyglycolide-polyvinyl alcohol, croscarmellose, polycaprolactone, EUDRAGIT® L100, EUDRAGIT® RS100, poly(ethylene glycol) 4000, poly(ethylene glycol) 8000 and poly(ethylene glycol) 20,000. In one example, the biodegradable active agent matrix can comprise poly(lactic-co-glycolide) having a copolymer ratio from 10/90 to 90/10 and in another case from 52/48 to 90/10. In yet other examples, the copolymer ratio can be from about 60/40 to about 40/60, or from about 55/45 to about 45/55. One particular aspect, the copolymer ratio can be about 50/50. In another specific example, the copolymer ratio can be 52-78/48-22 and in another specific example from 60-90/40-10. Although degradation rates can be dependent on such proportions, additional alternative approaches can also be useful such as device coatings, particle encapsulation, and the like.

Homogeneous delivery devices can be formed, for example, by mixing a polymer material with a loading amount of active agent to form a matrix dispersion or solution. The active agent can be homogeneously dispersed as a solid, dissolved uniformly, or partially dissolved as long as uniformity and homogeneity is maintained. Thus, in some examples, the active agent can be homogenously combined with the matrix such that the entire delivery device is homogenous or substantially homogenous. More specifically, the homogeneity can extend throughout the entire device such that the device consists essentially of the homogeneously mixed matrix and active agent along with optional additives. The loading amount can be chosen to correspond to the desired dosage during diffusion. Loading amount can take into account diffusion characteristics of the polymer and active agent, residual active agent, delivery time, and the like. The matrix dispersion can then be formed into the device shape using any suitable technique. For example, the matrix dispersion can be cast, sprayed and dried, extruded, stamped, or the like. Such configurations will most often be formed using a biodegradable matrix, although non-biodegradable materials can also be used. In one alternative formulation, the device can be formed in situ from a suspension of the active agent within a biodegradable polymer matrix precursor. Upon delivery into the target site, the biodegradable polymer matrix precursor can form (via precipitation and/or polymerization) the biodegradable active agent matrix in situ.

It is noted that with homogenous delivery devices, the shape and size of the delivery device can play an important role in the amount and rate of delivery of the active agent. For example, where a biodegradable active agent matrix is employed in the homogenous delivery device, the biodegradable matrix can generally accommodate various levels of active agent while maintaining a desirable biodegradation profile. The particular amount of active agent that a biodegradable matrix can controllably release within a particular biodegradation profile can depend on both the composition of the biodegradable matrix and the particular active agent being employed. Thus, in some examples, the particular composition of the homogenous delivery device can be somewhat constrained for a particular biodegradation profile and active agent combination.

Accordingly, the overall shape and size of the homogenous delivery device can be manipulated to accommodate faster and slower release rates and greater or smaller amounts of overall active agent released by the homogenous delivery device while maintaining suitable compositional parameters for a desired release profile. For example, in some cases, a large amount of a particular active agent can be required to provide a therapeutically effective amount to a subject to treat a particular condition. In such examples, the overall size of the homogenous delivery device can be increased to accommodate the large amount of active agent. Conversely, the overall size of the homogenous delivery device can be reduced where lesser amounts of the active agent are needed.

However, it is noted that, in some examples, increasing the size of the homogenous delivery device can also obstruct a line of sight in the eye. Thus, in some examples, the overall shape of the device can be manipulated to prevent obstruction of a line of sight in the eye. For example, in some cases, the homogenous delivery device can have a crescent shape, an ellipsoid shape (e.g. a disc shape, a football shape, an egg shape, or the like), a rod shape, or the like, to allow the size to increase to a greater extent along one axis relative to a perpendicular axis so as to not obstruct a line of sight in the eye.

Further, the shape of the homogenous delivery device can also affect the active agent release rate for the homogenous delivery device. For example, in some cases, a thinner homogenous delivery device can biodegrade more quickly than a thicker homogenous delivery device, resulting in a faster active agent release profile. Additionally, in some examples, the perimeter edges or other sections of the homogenous delivery device can be made thinner and/or rougher than other parts of the homogenous delivery device to provide an initial burst of active agent followed by a near zero order release profile. Further, in some examples, the overall geometrical shape alone of the homogenous delivery device can affect the release rate of the active agent. For example, exposed surface area to volume ratio can be increased to increase release rate and degradation.

With the above homogeneous delivery device, particular efficacy can be provided for treatment of uveitis and post-operative cataract surgery inflammation. For example, dexamethasone can be dispersed within a biodegradable active agent matrix. Although dexamethasone dosage amounts can vary, generally from about 100 mcg to about 400 mcg can be effective for these indications. More specifically, some patients may be categorized as low risk while others can be categorized as high risk due to various factors such as age, secondary complications, pre-existing conditions, etc. Most often, a low risk patient can benefit from a low dosage of about 100 mcg to about 150 mcg. In contrast, a high risk individual can be administered a high dosage of about 250 mcg to about 350 mcg. Some biodegradable implants can specifically designed and tested for the treatment of postoperative surgery inflammation and can deliver pharmaceutical active agent up to or about 2 weeks or more. Yet other biodegradable implants can be designed and tested for the treatment of postoperative surgery inflammation and uveitis and can deliver active agent up to or about 6-8 weeks or more. Further, depending on the severity of the inflammation, one, two, more implants can be implanted per eye during surgery.

The active agent delivery devices can optionally include additional active agents or other desired therapeutically beneficial substances. In one aspect, for example, the device can include at least one secondary active agent. Where a plurality of active agents is included in the active agent delivery device, the active agent matrix can be homogenous or non-homogenous. In some examples, the active agent delivery device can include a plurality of active agents and can be homogenous. In some examples, the active agent delivery device can include a plurality of active agents and can be non-homogenous. For example, one active agent can be coated on the surface of the implant. In yet other examples, the implant can be formulated to have pre-designated regions or layers including different active agents. In yet other examples, the implant can be formulated to have pre-designated regions or layers having the same active agent, but at different concentrations. For example, in some cases, an outer region or layer of the implant can have a higher concentration of the active agent to deliver a higher initial dose or burst of the active agent followed by a prolonged lower dose over a period of days or weeks. Further, in some examples, different regions of the implant can be adapted to biodegrade at different rates. In yet other examples, agents can optionally be coated on the implant to reduce the incidence of capsular fibrosis. Non-limiting examples of such agents include anti-cell proliferative agents, anti-TGF-beta agents, a5b1 integrin antagonists, rapamycin, and the like.

The ocular active agent delivery device can be configured to fit within a lens capsule or ciliary sulcus of an eye. The delivery device can be shaped in any geometry which allows for insertion into the lens capsule or ciliary sulcus. For example, the implant can be in the shape of round, square shape, crescent, or donut shape. However, other suitable shapes can include, but are not limited to, discs, pellets, rods, and the like. Although dimensions can vary, typical dimensions can range from about 0.5 mm to about 4 mm width and about 0.2 mm to about 1 mm thickness. Although the total mass of the delivery device can vary, most often the total mass can be from 0.2 mg to 4 mg, or from about 1.5 mg to about 2.5 mg. For example, about 2 mg total mass can provide effective active agent volume, while also balancing overall size to fit within the target tissue areas.

In some specific examples, the implant can be shaped as a disc or pellet. Where this is the case, the implant can typically have a diameter ranging from about 0.4 millimeters (mm) to about 3 mm, from about 0.5 mm to about 1.5 mm, or from about 0.7 mm to about 1.3 mm. Further, in some examples, the disc- or pellet-shaped implant can typically have a thickness ranging from about 0.2 mm to about 2 mm, from about 0.8 mm to about 1.5 mm, or from about 0.3 mm to about 1.0 mm. One example of a pellet or disc is illustrated in FIG. 1, which has a diameter of about 2 to 2.5 mm and a thickness of about 1.0-1.5 mm. In one specific example, the implant can have rounded edges, hemispherical, or semi-circular shapes.

In yet other specific examples, the implant can be shaped as a rod. Where this is the case, the implant can typically have a diameter ranging from about 0.05 mm to about 2 mm, from about 0.1 mm to about 1.0 mm, or from about 0.2 mm to about 0.8 mm. Further, in some examples, the rod-shaped implant can typically have a length ranging from about 0.5 mm to about 5 mm, from about 1.0 mm to about 3.0 mm, or from about 1.5 mm to about 2.5 mm.

Yet another aspect of the present invention provides a method of treating an eye condition. It is noted that when discussing various examples and embodiments of the implantable devices, systems, and methods described herein, each of these respective discussions can also apply to each of the other aspects of the present invention. Thus, for example, when discussing the implantable device per se, this discussion is also relevant to the methods discussed herein, and vice versa.

With this in mind, in some specific examples, the method can include inserting an intraocular active agent delivery device, as described herein, into the lens capsule or ciliary sulcus of an eye to deliver an active agent to the eye. In some examples, the intraocular active agent delivery device can include an active agent homogenously combined with a biodegradable active agent matrix such that the entire delivery device is homogenous. Further, in some examples, the delivery device can have a shape and size to provide a therapeutically effective amount of the active agent to the eye. Further still, in some examples, the delivery device can include a biodegradable active agent matrix that is formulated to provide sustained release of a therapeutically effective amount of the active during a release period. Where the delivery device includes a biodegradable active agent matrix, the biodegradable active agent matrix can be allowed to biodegrade to provide sustained release of the active agent to the eye during a release period.

In some examples, the intraocular active agent delivery device can provide an amount of the active agent to reduce retinal thickening associated with an ocular condition (e.g. cystoid macular edema) as compared to retinal thickening without treatment. In some further examples, sustained release of the amount of active agent can reduce retinal thickening associated with an ocular condition as compared to retinal thickening without treatment. Further, in some examples, for a subject in need thereof, treatment with the intraocular active agent delivery device can reduce retinal thickness by at least 10 µm, at least 20 µm, or more within 2 weeks or 1 week of insertion of the intraocular active agent delivery device into the eye as compared to the retinal thickness in the eye without treatment.

In some examples, the method can include performing a cataract removal surgery on the eye of the subject, further including removing an existing lens from the eye of the subject, inserting an intraocular lens into the eye of the subject, and placing the biodegradable active agent matrix within the lens capsule. In some examples, the biodegradable active agent matrix or implant can be associated with the intraocular lens. Where this is the case, the delivery device may be attached or detached from an intraocular lens. The delivery device can be associated by actual contact or sufficient proximity while allowing effective diffusion of active agent to target areas of the eye. A biodegradable system can have substantial value in routine cataract surgery to provide short-term/time-limited delivery of postoperative medicines while minimizing or eliminating the need for eyedrop usage by the patient. The lens that is removed can be the original natural lens of the eye, or it can be a lens that was previously inserted into the eye as a result of a prior procedure.

Numerous methods of placing the device into the eye are contemplated. For example, in one aspect, the implant can be associated with the intraocular lens prior to inserting the intraocular lens into the eye. In such cases it can be necessary to configure the implant to comply with any requirements of the surgical procedure. For example, cataract surgeries are often performed through a small incision. One standard size incision is about 2.75 mm; although this device can be compatible with smaller or larger incision sizes as well. As such, the intraocular lens assembly can be shaped to allow insertion through this small opening. Thus the active agent delivery device can also be configured to be inserted with the intraocular lens assembly, e.g. by shape and/or choice of resilient and flexible material for the implant. Additionally, the active agent delivery device can also be physically coupled or decoupled to the intraocular lens assembly prior to insertion of the assembly into the eye. In another aspect, the implant can be positioned within the lens capsule, and optionally associated with the intraocular lens assembly, following insertion of the lens into the eye. The capsular bag can be readily reopened for a patient having prior cataract surgery. Thus, the insertion of the delivery device can be performed immediately prior to insertion of an intraocular lens or later in time as a separate procedure.

EXAMPLES

Example 1

A standard clear-corneal phacoemulsification with intraocular lens (ACRYSOF® SA60AT; Alcon Laboratories, Inc.) implantation was performed on 35 rabbits. At the time of each surgery, an intraocular device containing an active agent was inserted into a lens capsule of each rabbit. The rabbits were divided into 4 groups, depending on the active agent in the intraocular device. Devices were loaded with 5-15 mg of either AVASTIN®, Timolol, Brimonidine, or Latanoprost. Each group was evaluated to determine the intraocular device and lens stability, capsular fibrosis, and healing of cataract wounds and anterior segment. A subgroup of eyes was evaluated weekly for 4 weeks for inflammation and harvested at 1 month for histopathologic evaluation of capsular and CDR integrity.

Example 2

The surgery and setup as described in Example 1 was repeated, with the exception that aqueous and vitreous taps were performed biweekly and assayed for drug concentrations with HPLC and/or ELISA. In each drug group, half of the eyes were harvested at one month and the other half at two months. This was accomplished as follows: immediately after sacrificing the rabbit and enucleating the eye, the eye was frozen in liquid nitrogen to prevent perturbation and redistribution of drug in eye tissues. The eye was then dissected into 3 parts (aqueous humor, vitreous and retina/choroid layer) to evaluate anatomic toxicity and tissue drug concentration. The intraocular device was retrieved and assessed for remaining drug amounts. The distribution profile of the intraocular device was compared with the conventional intravitreal injection of 2.5 mg/0.1 cc AVASTIN® for direct comparison of the different delivery methods.

At 2 and 4 months, eyes from the remaining subgroups of rabbits were enucleated, fixed by 10% formalin, embedded in paraffin, step sectioned, stained by hematoxyline and eosin (H & E), and examined for histological changes.

Example 3

Three intraocular devices were implanted into eyes of New Zealand white rabbits under general anesthesia after lens extraction (phacoemulsification technique). Two of the devices were loaded with AVASTIN® and one was loaded with the contrast agent Galbumin as a control. Proper intraocular device position was verified by MRI as well as clinical examination.

Figure 5:
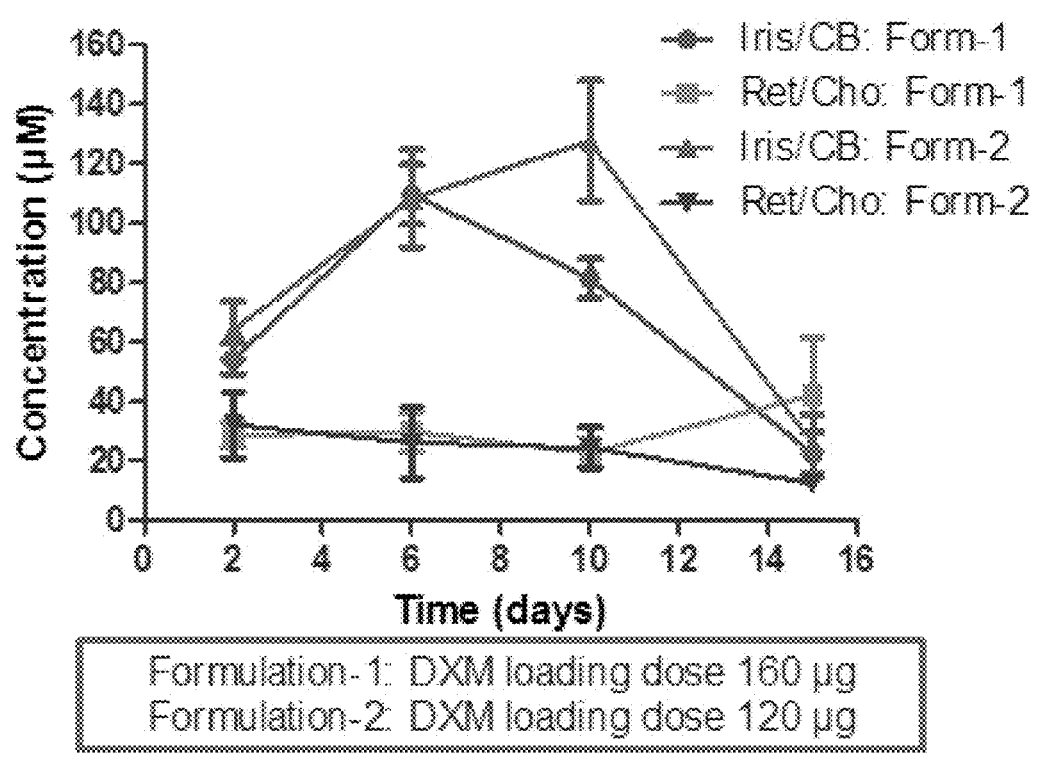
FIG. 5 time vs concentration profile of an example BDI implant with 120 to 160 µg of DXM in iris/ciliary body and retina/choroid of NZW rabbits.
Figure 6:
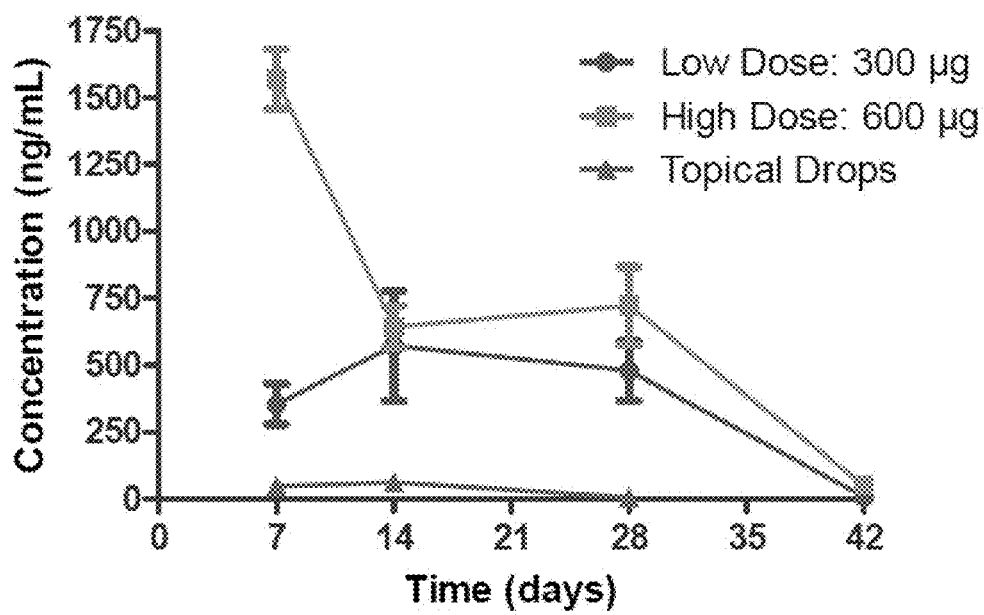
FIG. 6 is a graph of time vs. concentration profile of an example BDI implant and topical drops in aqueous humor of New Zealand white rabbits.

The rabbits were sacrificed and the eyes are removed and assayed after 1 week post implantation. AVASTIN® was detected by ELISA in the retina and vitreous at concentrations of 24-48 mcg/mL, and was not present in the control rabbit eye. FIG. 5 shows the amount of AVASTIN® assayed per ocular region at 1 week post implantation.

Example 4

To confirm that placement of implant in the capsular bag and delivers drugs both to the front and back of the eye for short and long term, microparticles were prepared using PLGA [poly(d,l-lactide-co-glycolide), MW. 7000-17000, acid terminated], hydroxypropyl methyl cellulose (HPMC) and dexamethasone. Dexamethasone loaded PLGA microspheres were prepared using standard oil-in-water (o/w) emulsion-solvent extraction method. An amount of 160 mg PLGA was dissolved in 4 mL methylene chloride and 1 mL acetonitrile. An amount of 40 mg dexamethasone and 10 mg of HPMC was dispersed in the PLGA solution by vortexing for 5 min. This organic phase was then emulsified in 20 mL of a 2% (w/v) PVA (MW 90 kDa) solution and homogenized. The resultant emulsion was poured into 200 mL of a 2.0% (w/v) PVA (MW 90 kDa) solution and stirred in an ice bath for 6 min. The contents were stirred for 8 hr at room temperature to evaporate the dichloromethane and acetonitrile to form a turbid microparticulate suspension. The microparticles were separated by centrifugation, washed twice, resuspended in deionized water, and freeze-dried to obtain lyophilized particles. The prepared microparticles were characterized and pelleted using bench top pellet press with 2 mm die set to form an implant.

These implants were sterilized, implanted in the capsular bag of rabbit's eyes. Two dose groups were used (300 and 600 µg), two rabbits were sacrificed from each of low and high dose group at 1, 2, 4, 6 weeks and various tissue samples (aqueous humor, vitreous humor, IOL, iris/ciliary body and retina/choroid) were collected and samples were analyzed by a validated LC/MS/MS method. Micro spheres were in the range of 6±2 µM as confirmed by ZETA-SIZER™ nano and SEM photomicrographs. Drug loading in the microparticles was >99% and the final yield was 60% (i.e. encapsulation efficiency). Drug loading was determined as percent drug loading=(weight of drug loaded/weight of microspheres)×100. Dose related pharmacokinetics with near zero order kinetics was observed in rabbits up to 6 weeks. Further, dexamethasone flow was bidirectional from the endocapsular space into both the anterior and posterior chambers. There were also no cells or formation of fibrin in the anterior and posterior chambers of the eye. Histological examinations revealed all the tissues examined were normal and showed no signs of inflammation.

All the study animals were acquainted to study room conditions once they are out of quarantine and randomized. All the positive control group and implantation groups underwent phacoemulsification and insertion of an intraocular lens (IOL) in both the eyes. Group III and IV received one and two implants per eye respectively.

Group I: Normal control group; n=6
Group II: Phacoemulsification and inserting IOL; DXM drops (up to 4 weeks with tapering) and antibiotic drops (up to 2 days); positive control group; n=6
Group-III: Phacoemulsification and inserting IOL; BDI implant low dose (one implant per eye) and antibiotic drops up to 2 days (b.i.d.) after surgery; n=8
Group-IV: Phacoemulsification and inserting IOL; BDI implant high dose (two implants per eye) and antibiotic drops up to 2 days (b.i.d.) after surgery, n=8

Figure 10:
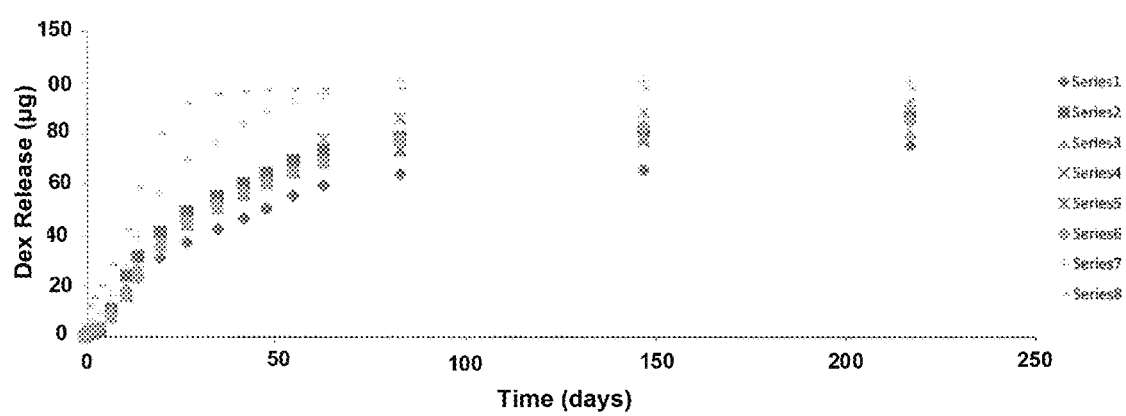
FIG. 10 is a graph illustrating the effect of croscarmellose concentration on drug release for some example BDI implants.

Results of in vitro release kinetics are presented in FIG. 10. All the batches exhibited biphasic release pattern with initial burst release on day-1 and thereafter slow and sustained release. The burst effect was slightly higher with implants containing HPMC.

A total of 16 animals (32 eyes) received the implant. Dexamethasone concentrations are presented in FIG. 11 through FIG. 14. The implants degraded slowly over 4 weeks and by week 6 were completely disappeared. Therapeutic concentrations of DXM was found up to week 6 with minimal systemic exposure (<40 ng/mL with high dose), whereas, with dexamethasone drops systemic exposure was higher (>150 ng/mL during week 1). Mean PK parameters for BDI-2 implant and positive control group in aqueous humor, vitreous humor, retina/choroid, and iris/ciliary body are shown in Table 1 and 2.

TABLE 1

| | Pharmacokinetics in aqueous humor and vitreous humor | | | | | |
|---|---|---|---|---|---|---|
| | Low dose: 300 µg | | High dose: 600 µg | | Dexamethasone Drops | |
| Parameter | Aqueous humor | Vitreous humor | Aqueous humor | Vitreous humor | Aqueous humor | Vitreous humor |
| $C_{max\ (ng/mL)}$ | 650 ± 109 | 892 ± 151 | 1570 ± 113 | 1379 ± 233 | 62 ± 24 | 3 ± 0 |
| $T_{max\ (day)}$ | 19 ± 8 | 28 ± 0 | 7 ± 0 | 28 ± 0 | 14 ± 0 | 16 ± 11 |

TABLE 1-continued

Pharmacokinetics in aqueous humor and vitreous humor

| Parameter | Low dose: 300 μg | | High dose: 600 μg | | Dexamethasone Drops | |
|---|---|---|---|---|---|---|
| | Aqueous humor | Vitreous humor | Aqueous humor | Vitreous humor | Aqueous humor | Vitreous humor |
| $AUC_{0-t\ (day*ng/mL)}$ | 15231 ± 361 | 18317 ± 2435 | 28202 ± 3369 | 32933 ± 4027 | 1023 ± 320 | 61 ± 5 |
| $C_{last\ (ng/mL)}$ | 8 ± 3 | 2 ± 1 | 52 ± 18 | 85 ± 23 | 6 ± 2 | 2 ± 1 |

TABLE 2

Pharmacokinetics in retina/choroid and iris/ciliary body

| Parameter | Low dose: 300 μg | | High dose: 600 μg | | Dexamethasone Drops | |
|---|---|---|---|---|---|---|
| | Retina/Choroid | Iris/CB | Retina/Choroid | Iris/CB | Retina/Choroid | Iris/CB |
| $C_{max\ (\mu M)}$ | 21 ± 4 | 35 ± 5 | 117 ± 40 | 209 ± 24 | 3 ± 1 | 3 ± 2 |
| $T_{max\ (day)}$ | 14 ± 0 | 7 ± 0 | 23 ± 8 | 14 ± 0 | 14 ± 0 | 9 ± 4 |
| $AUC_{0-t\ (day*\mu M)}$ | 455 ± 61 | 759 ± 132 | 2226 ± 1105 | 3913 ± 685 | 48 ± 16 | 42 ± 27 |
| $C_{last\ (\mu M)}$ | 1.3 ± 0.6 | 1.5 ± 0.5 | 12 ± 8 | 13 ± 10 | 0.2 ± 0.1 | 0.5 ± 0.3 |

Intraocular pressure was normal in all the groups. Further, there were no signs of anterior or posterior chamber inflammation as assessed with Slit lamp biomicroscopy and confirmed by histological examination. There was a trend in increase in retinal thickness in animals treated with dexamethasone drops whereas, implants maintained retinal thickness.

The PLGA polymer degrades in to lactic and glycolic acid through hydrolysis, then further degrades in to carbon dioxide and water before eliminating from the body. Implants did not migrate to the center to obstruct the visual field.

BDI-1 implant was manufactured by following partial solvent casting method with subsequent evaporation and removing the residual solvent by drying the product under high vacuum for 3 days. Various implants were prepared using PLGA [poly(d,l-lactide-co-glycolide), MW. 7000-17000, acid terminated], hydroxypropyl methyl cellulose (HPMC), croscarmellose sodium (cross linked sodium carboxymethylcellulose), hydroxypropyl cellulose and dexamethasone in several different compositions.

The dried particles were directly pelleted using bench top pellet press with a 2 mm die set to form an implant.

The selected BDI-1 implants (from in-vitro release studies, FIG. 7) were sterilized, implanted in the capsular bag of rabbit's eyes. Two implants with different composition and dose were tested in-vivo in NZW rabbits to establish pharmacokinetics. Two rabbits were sacrificed at 2, 6, 10, 15 days and various tissue samples (aqueous humor, vitreous humor, IOL, iris/ciliary body and retina/choroid) were collected and samples were analyzed by a validated LC/MS/MS method. Pharmacokinetics with near zero order kinetics was observed in rabbits up to 15 days. Further, dexamethasone flow was bidirectional from the endocapsular space into both the anterior and posterior chambers. There were also no cells or formation of fibrin in the anterior and posterior chambers of the eye. Histological examinations revealed all the tissues examined were normal and showed no signs of inflammation.

Figure 7:
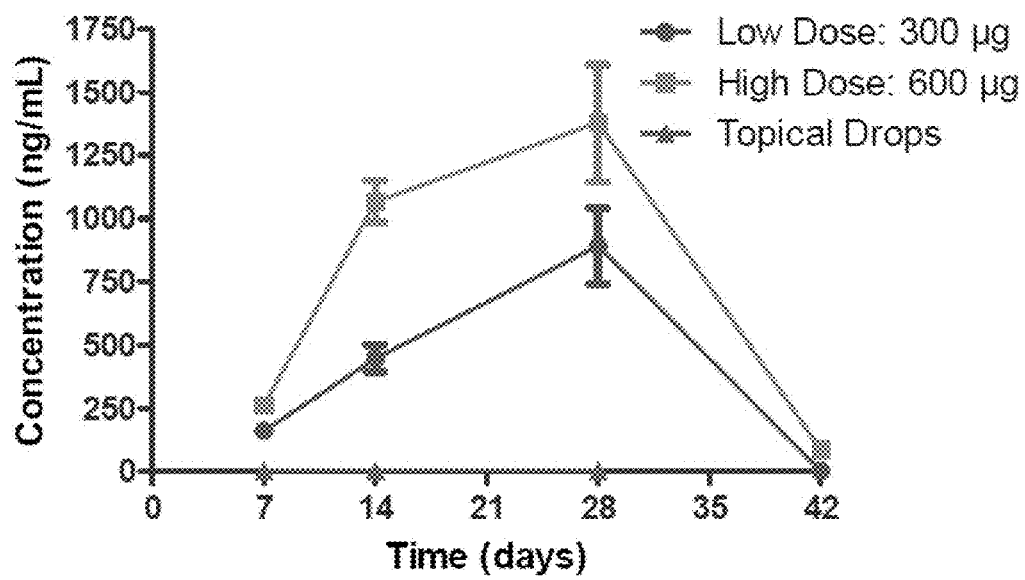
FIG. 7 is a graph of time vs. concentration profile of an example BDI implant and topical drops in vitreous humor of New Zealand white rabbits.

Results of in vitro release kinetics are presented in FIG. 7. All the batches exhibited smooth release pattern with initial burst release on day-1 and thereafter slow and sustained release. The burst effect was slightly higher with implants containing HPMC.

Figure 8:
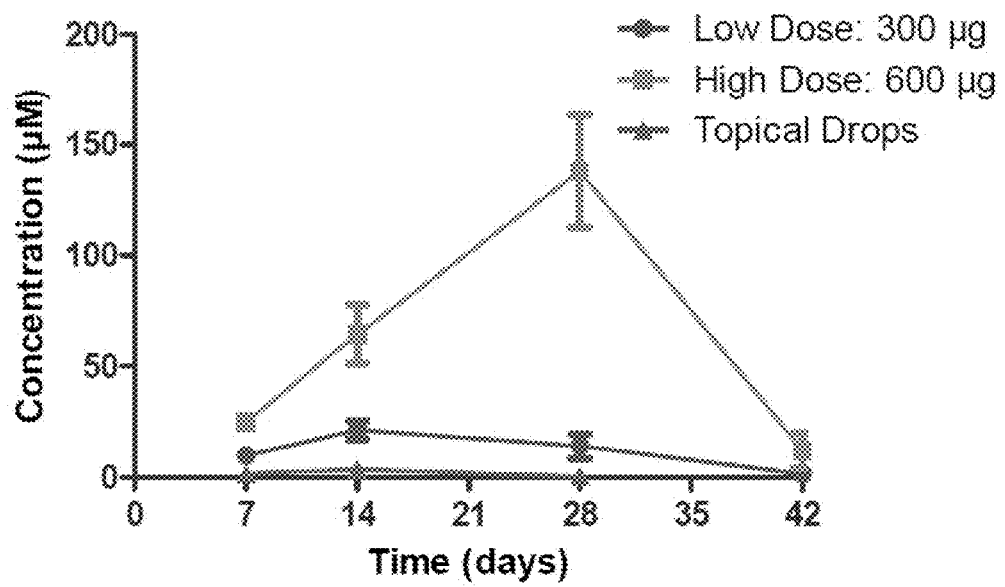
FIG. 8 is a graph of time vs. concentration profile of an example BDI implant and topical drops in retina/choroid of New Zealand white rabbits.
Figure 9:
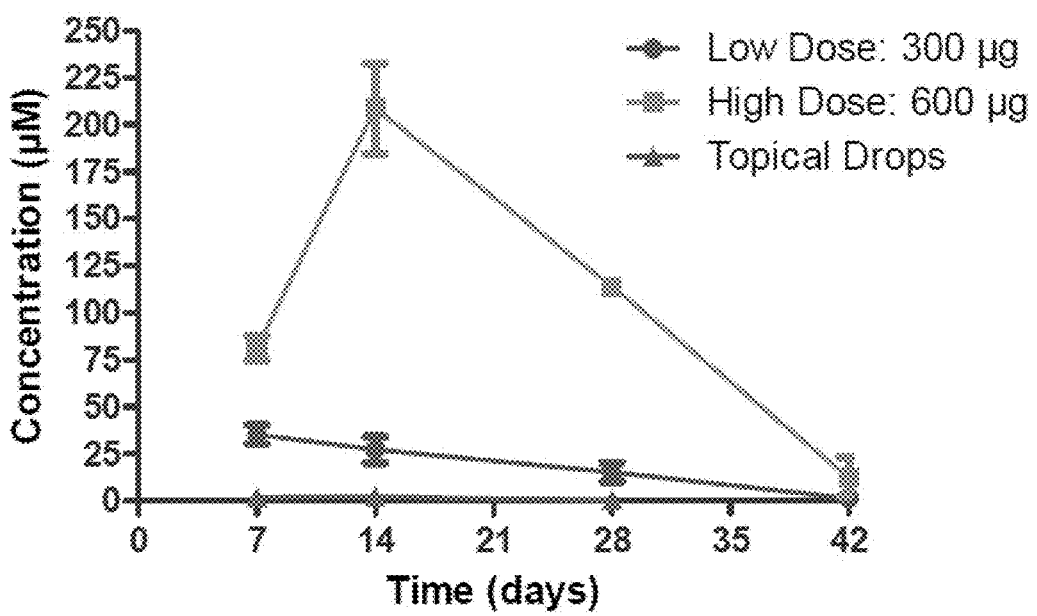
FIG. 9 is a graph of time vs. concentration profile of an example BDI implant and topical drops in iris/ciliary body of New Zealand white rabbits.

A total of 8 animals (16 eyes) received the implant containing 120 μg of DXM. DXM concentrations are presented in FIG. 8 FIG. 9. The implants eroded slowly over 10 days and reaching trough concentrations of DXM by day 15. The implants are degraded by 80% of its mass by day 15 and expected to fully degrade by day 20. Therapeutic concentrations of DXM was found up to day 15 with minimal systemic exposure (<23 ng/mL), whereas, with dexamethasone drops systemic exposure was higher (>150 ng/mL during week 1, in-house data).

Example 5

A number of biodegradable implants were prepared with PLGA, croscarmellose sodium, and dexamethasone in accordance with Table 3 below.

TABLE 3

Effect of CrosCarmellose on Drug Release Rate

| Formulation | PLGA (wt %) | Croscarmellose (wt %) | Dexamethasone (wt %) |
|---|---|---|---|
| Series 1 | 85 | 0 | 15 |
| Series 2 | 84 | 1 | 15 |
| Series 3 | 83.5 | 1.5 | 15 |
| Series 4 | 83 | 2 | 15 |
| Series 5 | 82.5 | 2.5 | 15 |
| Series 6 | 82 | 3 | 15 |
| Series 7 | 80 | 5 | 15 |
| Series 8 | 77.5 | 7.5 | 15 |

Drug release profiles for each of the listed formulations were obtained using an in-vitro drug release model. Individual drug release profiles are presented in FIG. 10. As illustrated in FIG. 10, increasing amounts of croscarmellose can increase the drug release rate from the biodegradable implant as compared to a biodegradable implant prepared with only PLGA.

Example 6

Figure 11:
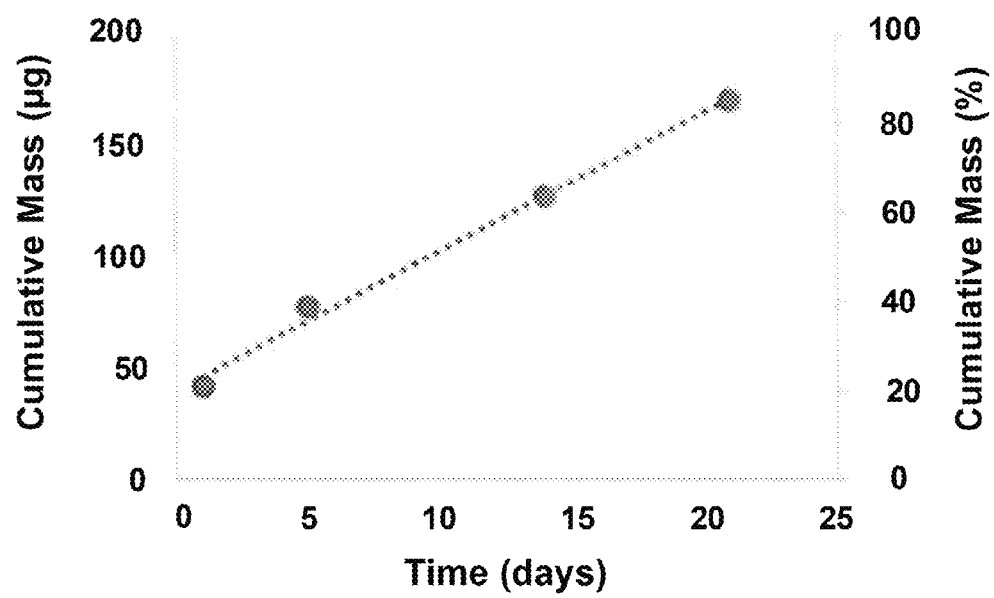
FIG. 11 is a graph of in-vitro release kinetics of an example BDI implant. Data are presented as mean±SD (n=3).
Figure 12:
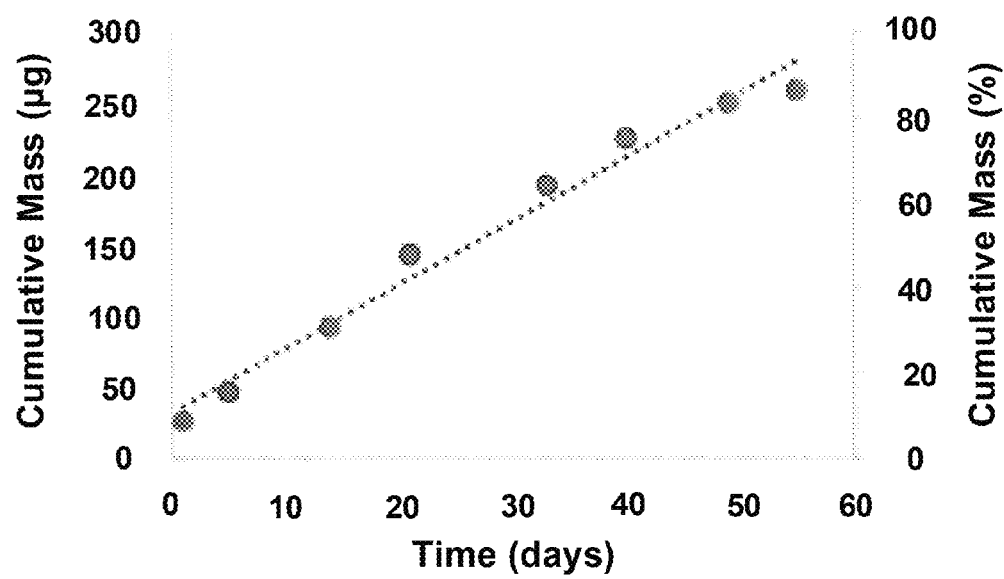
FIG. 12 is a graph of in-vitro release kinetics of another example BDI implant. Data are presented as mean±SD (n=3).
Figure 13:
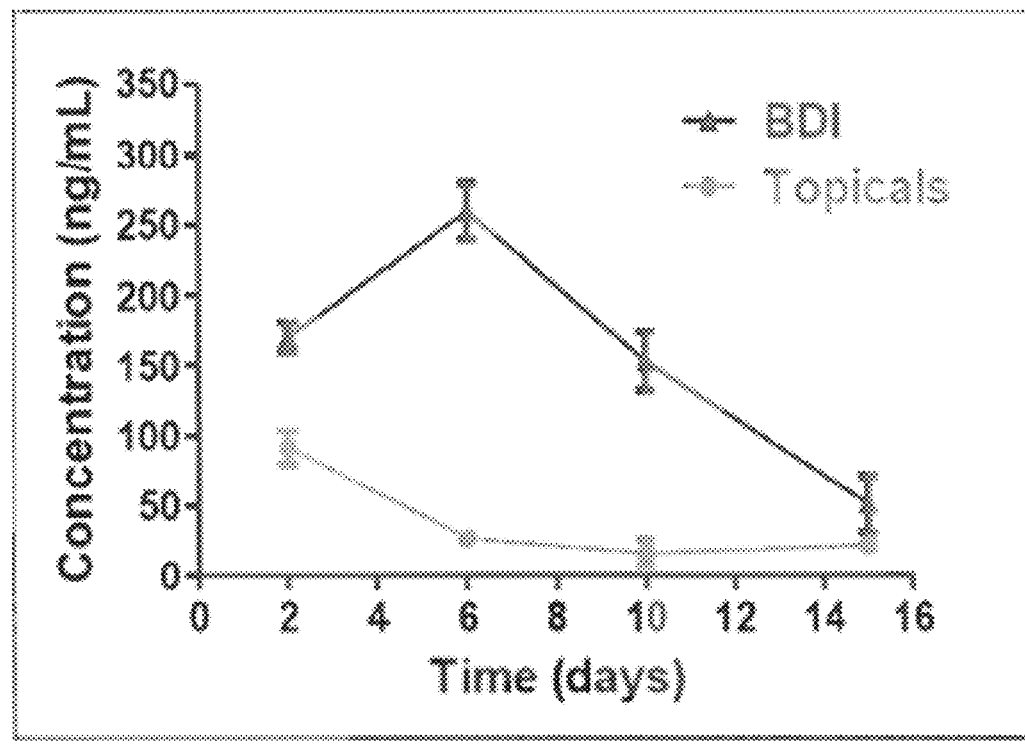
FIG. 13 is a graph of time vs. concentration profile of an example BDI implant and topical drops in aqueous humor of New Zealand white rabbits.
Figure 14:
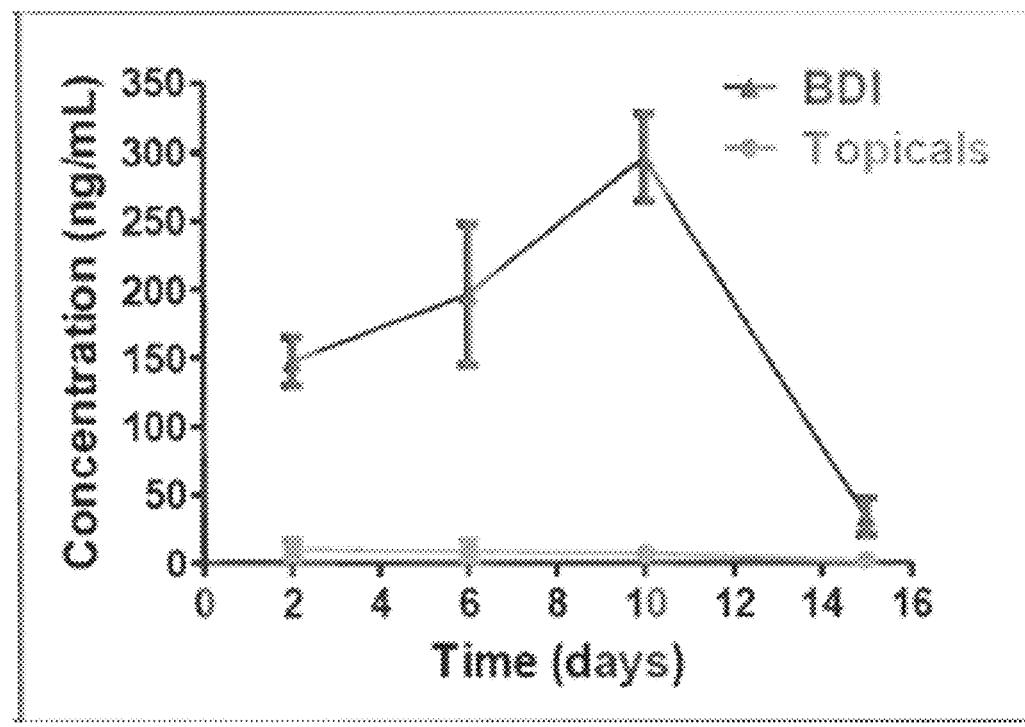
FIG. 14 is a graph of time vs. concentration profile of an example BDI implant and topical drops in vitreous humor of New Zealand white rabbits.
Figure 15:
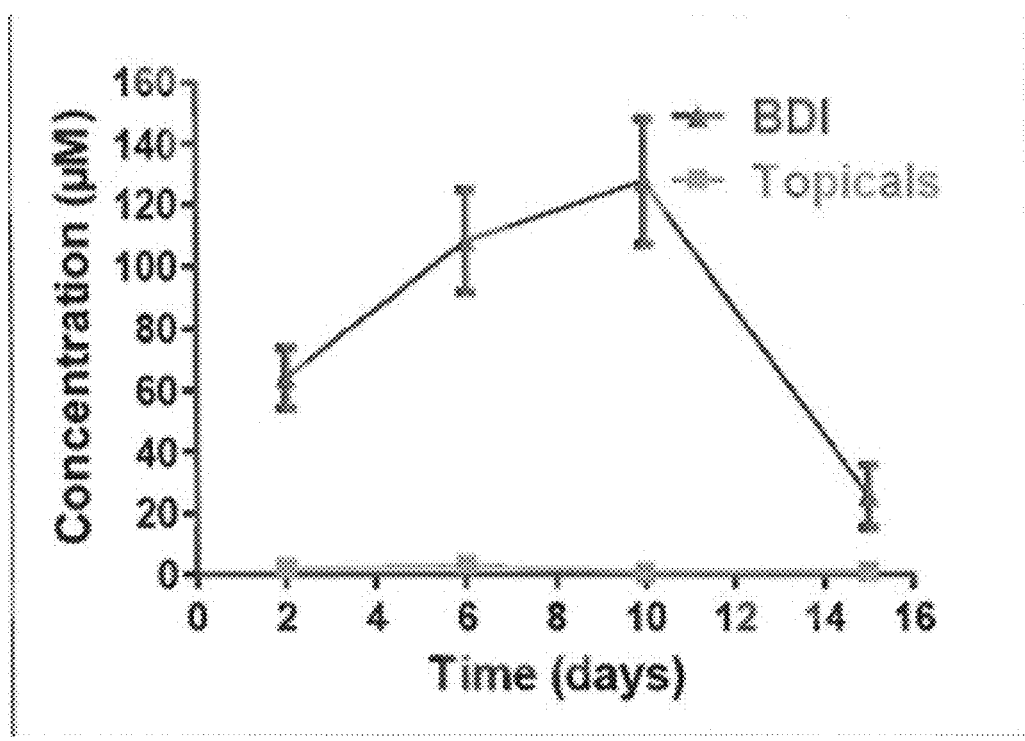
FIG. 15 is a graph of time vs. concentration profile of an example BDI implant and topical drops in retina/choroid of New Zealand white rabbits.
Figure 16:
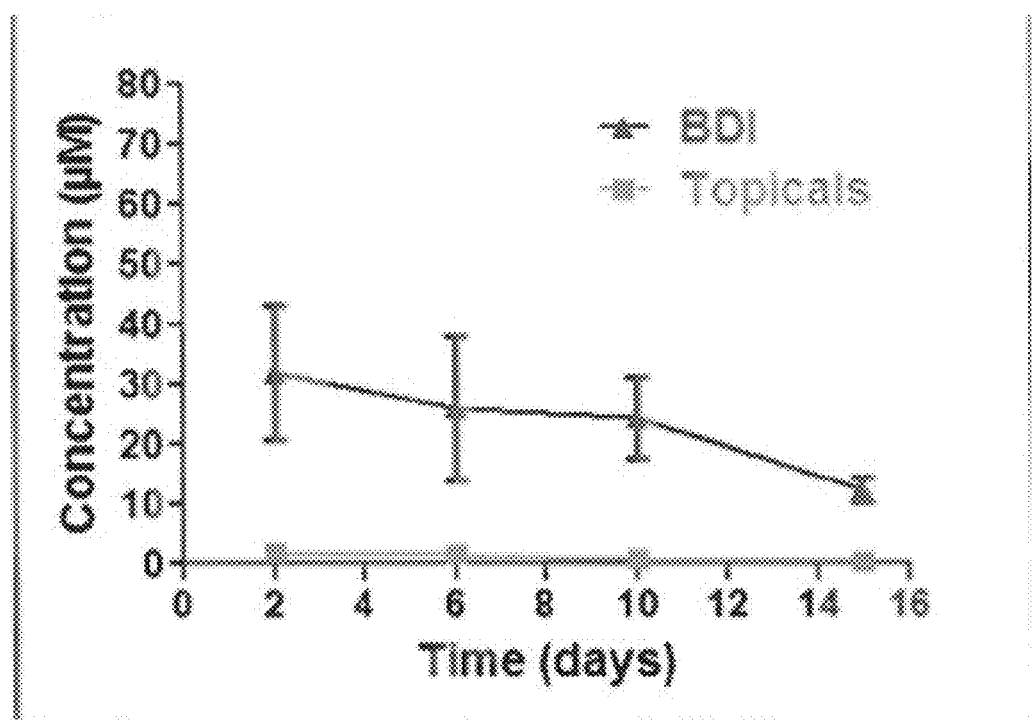
FIG. 16 is a graph of time vs. concentration profile of an example BDI implant and topical drops in iris/ciliary body of New Zealand white rabbits.

Two biodegradable dexamethasone implants (BDI) were prepared using different formulations including PLGA, croscarmellose, and dexamethasone. The first BDI was configured to deliver 200 mcg dexamethasone over a period of two weeks. The second BDI was configured to deliver 300 mcg dexamethasone over a period of six weeks. The drug release profiles were evaluating using an in-vitro drug release model. The release profile for the first and second BDIs are illustrated in FIGS. 11 and 12, respectively.

Further, these implants were sterilized and implanted in the capsular bag of rabbit's eyes. The implants degraded slowly over a number of weeks until they completely disappeared. Mean PK parameters for the first BDI implant and positive control group in aqueous humor, vitreous humor, retina/choroid, and iris/ciliary body are shown in Tables 4 and 5.

TABLE 4

Pharmacokinetics in aqueous humor and vitreous humor for first BDI

| Parameter | BDI: 200 μg | | Dexamethasone Drops | |
|---|---|---|---|---|
| | Aqueous humor | Vitreous humor | Aqueous humor | Vitreous humor |
| $C_{max}$ (ng/mL) | 259 ± 20 | 296 ± 32 | 92 ± 12 | 15 ± 4 |
| $T_{max}$ (day) | 6 ± 0 | 10 ± 0 | 2 ± 0 | 3 ± 2 |
| $AUC_{0-t}$ (day*ng/mL) | 2365 ± 182 | 2769 ± 276 | 517 ± 43 | 104 ± 42 |
| $C_{last}$ (ng/mL) | 52 ± 20 | 34 ± 14 | 23 ± 6 | 1 ± 1 |

TABLE 5

Pharmacokinetics in retina/choroid and iris/ciliary body for first BDI

| Parameter | BDI: 200 μg | | Dexamethasone Drops | |
|---|---|---|---|---|
| | Retina/Choroid | Iris/CB | Retina/Choroid | Iris/CB |
| $C_{max}$ (μm) | 133 ± 12 | 38 ± 6 | 3.3 ± 0.8 | 2.2 ± 0.5 |
| $T_{max}$ (day) | 9 ± 2 | 6 ± 4 | 6 ± 0 | 3 ± 2 |
| $AUC_{0-t}$ (day*μM) | 1264 ± 66 | 312 ± 46 | 23 ± 4 | 19 ± 8 |
| $C_{last}$ (μM) | 26 ± 10 | 16 ± 6 | 0.9 ± 0.2 | 0.6 ± 0.2 |

Figure 17:
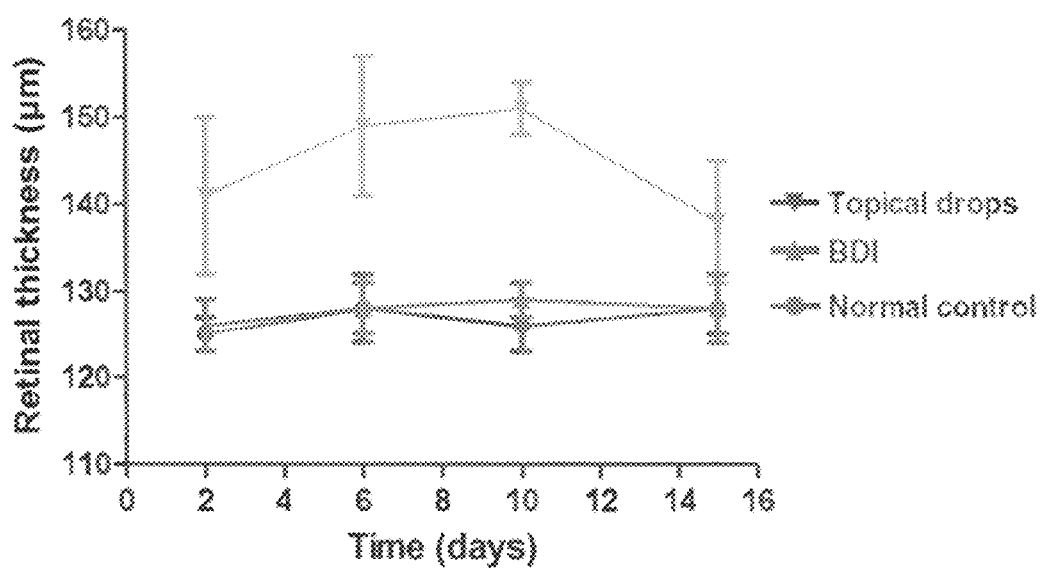
FIG. 17 is a graph of retinal thickness vs. time profile of an example BDI implant and topical drops as compared to normal control.
Figure 18:
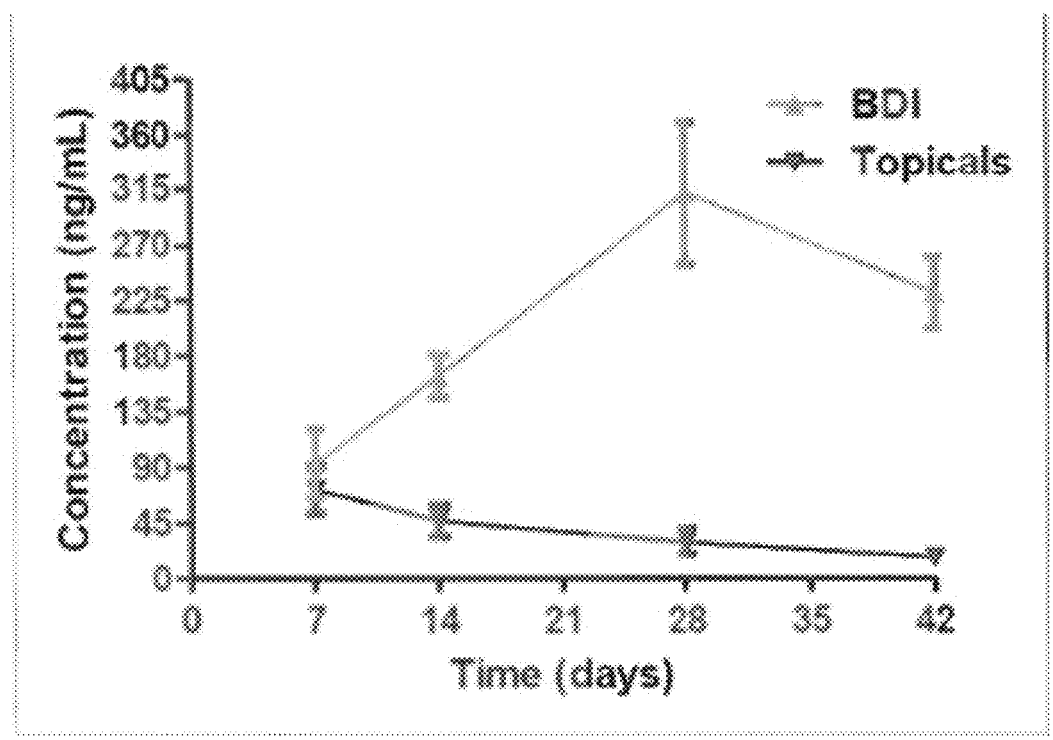
FIG. 18 is a graph of time vs. concentration profile of an example BDI implant and topical drops in aqueous humor of New Zealand white rabbits.
Figure 19:
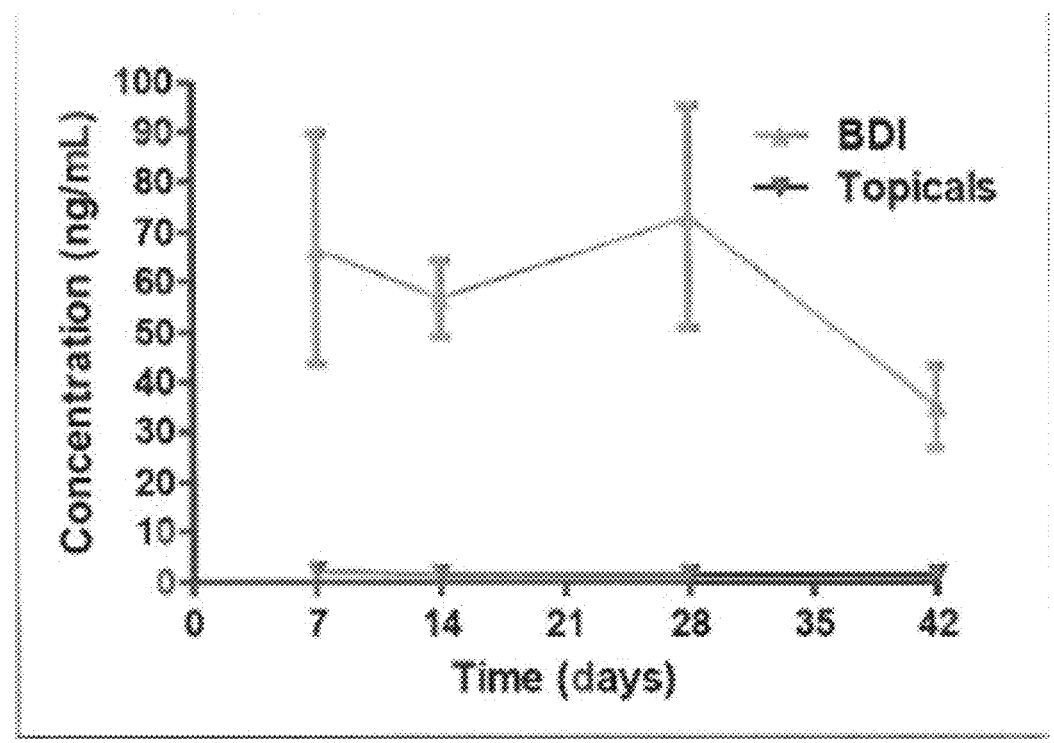
FIG. 19 is a graph of time vs. concentration profile of an example BDI implant and topical drops in vitreous humor of New Zealand white rabbits.
Figure 20:
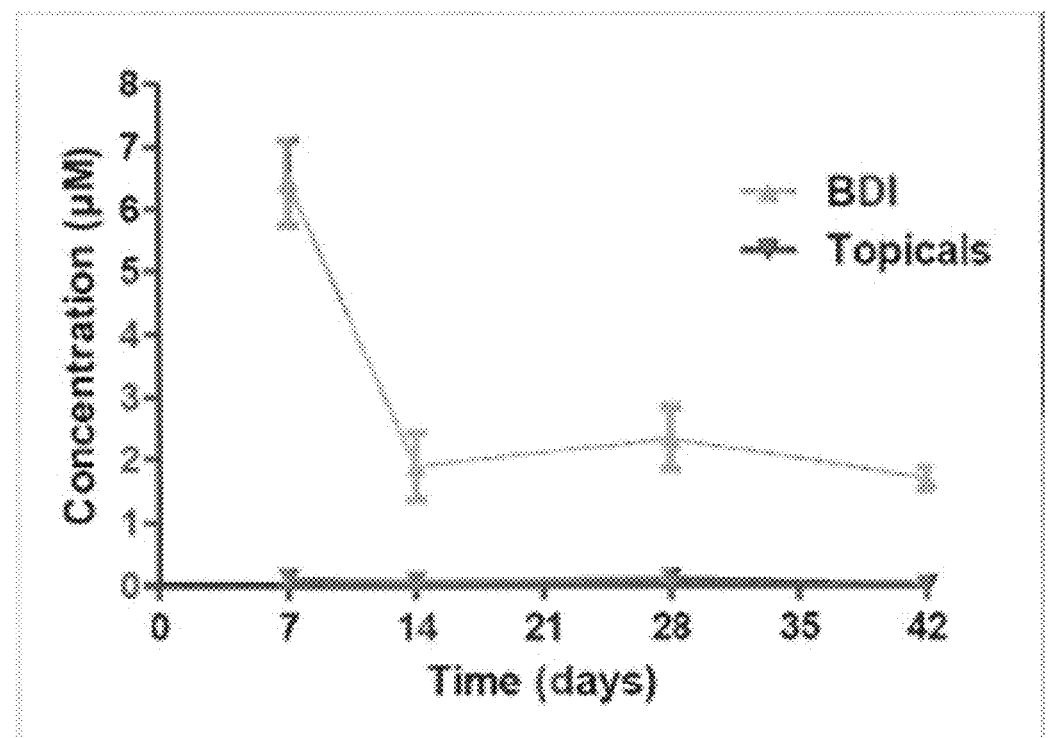
FIG. 20 is a graph of time vs. concentration profile of an example BDI implant and topical drops in retina/choroid of New Zealand white rabbits.
Figure 21:
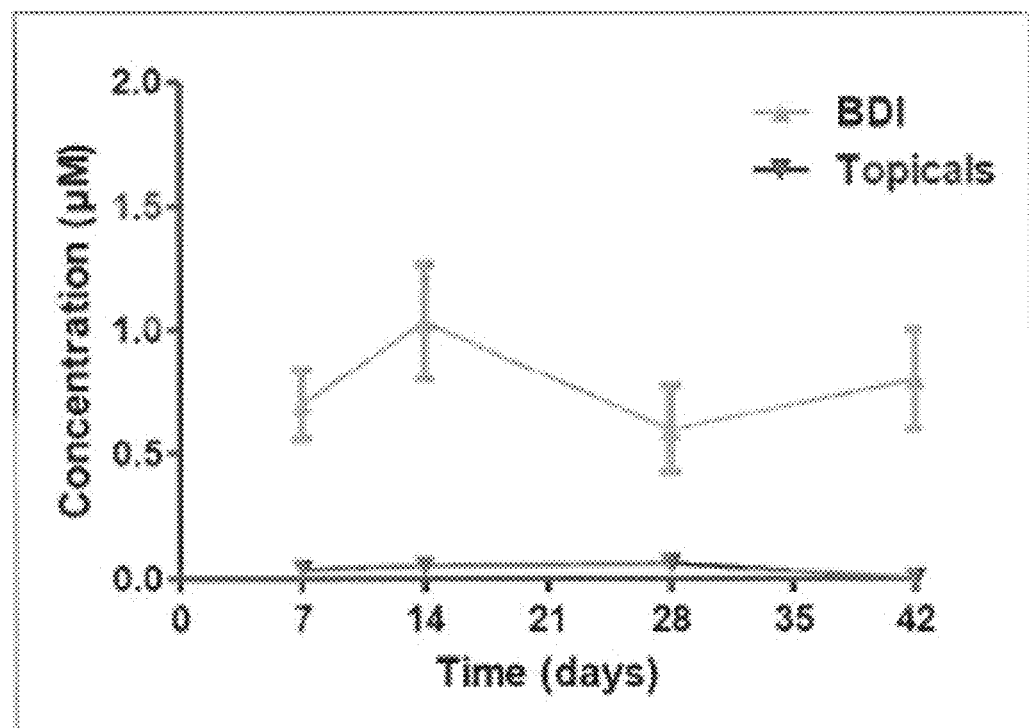
FIG. 21 is a graph of time vs. concentration profile of an example BDI implant and topical drops in iris/ciliary body of New Zealand white rabbits.

Dexamethasone concentration profiles for each of the ocular regions are presented in FIG. 13 through FIG. 16. Further, the retinal thicknesses for each of the test subjects were measured over time and compared to retinal thicknesses for test subjects treated with a topical formulation and control subjects with normal retinal thickness. These results are depicted in FIG. 17. As illustrated in FIG. 17, a therapeutically effective dose can reduce retinal thickening associated with an ocular condition as compared to retinal thickening without treatment or as compared to treatment with a topical formulation.

Mean PK parameters for the second BDI implant and positive control group in aqueous humor, vitreous humor, retina/choroid, and iris/ciliary body are shown in Tables 6 and 7.

TABLE 6

Pharmacokinetics in aqueous humor and vitreous humor for second BDI

| Parameter | BDI: 300 μg | | Dexamethasone Drops | |
|---|---|---|---|---|
| | Aqueous humor | Vitreous humor | Aqueous humor | Vitreous humor |
| $C_{max}$ (ng/mL) | 314 ± 55 | 86 ± 10 | 72 ± 19 | 2.2 ± 0.3 |
| $T_{max}$ (day) | 28 ± 0 | 21 ± 12 | 7 ± 0 | 9 ± 4 |
| $AUC_{0-t}$ (day*ng/mL) | 8377 ± 1055 | 2329 ± 219 | 1533 ± 325 | 68 ± 5 |
| $C_{last}$ (ng/mL) | 232 ± 29 | 35 ± 8 | 17 ± 8 | 2 ± 1 |

TABLE 7

Pharmacokinetics in retina/choroid and iris/ciliary body for second BDI

| Parameter | BDI: 300 μg | | Dexamethasone Drops | |
|---|---|---|---|---|
| | Retina/Choroid | Iris/CB | Retina/Choroid | Iris/CB |
| $C_{max}$ (μm) | 6.4 ± 0.7 | 1.1 ± 0.2 | 0.13 ± 0.06 | 0.06 ± 0.01 |
| $T_{max}$ (day) | 7 ± 0 | 14 ± 0 | 14 ± 12 | 23 ± 8 |
| $AUC_{0-t}$ (day*μM) | 99 ± 19 | 28 ± 6 | 2.3 ± 0.7 | 1.2 ± 0.2 |
| $C_{last}$ (μm) | 1.7 ± 0.2 | 0.8 ± 0.2 | 0.11 ± 0.06 | 0.06 ± 0.01 |

Figure 22:
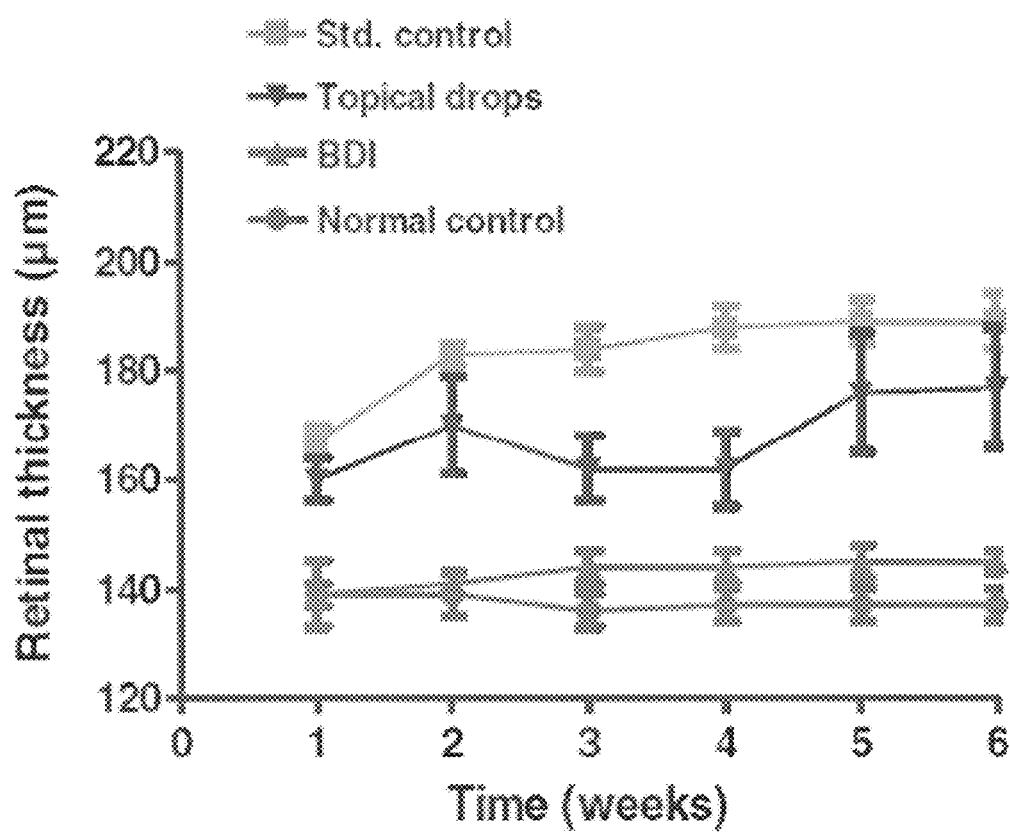
FIG. 22 is a graph of retinal thickness vs. time profile of an example BDI implant and topical drops as compared to normal control. These drawings merely depict exemplary embodiments of the present invention and they are, therefore, not to be considered limiting of its scope. It will be readily appreciated that the components of the present invention, as generally described and illustrated in the figures herein, could be arranged, sized, and designed in a wide variety of different configurations.

Dexamethasone concentration profiles for each of the ocular regions are presented in FIG. 18 through FIG. 21. Further, the retinal thicknesses for each of the test subjects were measured over time and compared to retinal thicknesses for test subjects treated with a topical formulation and control subjects with normal retinal thickness. These results are depicted in FIG. 22. As illustrated in FIG. 22, a therapeutically effective dose can reduce retinal thickening associated with an ocular condition as compared to retinal thickening without treatment or as compared to treatment with a topical formulation.

Example 7

A number of biodegradable implants were prepared with PLGA, croscarmellose sodium, and dexamethasone in accordance with Table 8 below.

TABLE 8

Effect of CrosCarmellose on Drug Release Rate

| Formulation | PLGA (wt %) | Croscarmellose (wt %) | Dexamethasone (wt %) |
|---|---|---|---|
| Series 9 | 66 | 4 | 30 |
| Series 10 | 64 | 6 | 30 |
| Series 11 | 62 | 8 | 30 |
| Series 12 | 67.5 | 10 | 22.5 |
| Series 13 | 65 | 12.5 | 22.5 |
| Series 14 | 62.5 | 15 | 22.5 |
| Series 15 | 60 | 17.5 | 22.5 |
| Series 16 | 57.5 | 20 | 22.5 |
| Series 17 | 70 | 20 | 10 |
| Series 18 | 79 | 6 | 15 |
| Series 19 | 78 | 7 | 15 |
| Series 20 | 85 | 0 | 15 |
| Series 21 | 84 | 1 | 15 |
| Series 22 | 83 | 1.5 | 15 |
| Series 23 | 83 | 2 | 15 |
| Series 24 | 82.5 | 3 | 15 |
| Series 25 | 81 | 4 | 15 |
| Series 26 | 80 | 4.5 | 15 |

TABLE 8-continued

Effect of CrosCarmellose on Drug Release Rate

| Formulation | PLGA (wt %) | Croscarmellose (wt %) | Dexamethasone (wt %) |
|---|---|---|---|
| Series 27 | 80 | 5 | 15 |
| Series 28 | 77.5 | 7.5 | 15 |

Drug release profiles for each of the listed formulations were obtained using an in-vitro drug release model. Notably, lower croscarmellose percentages increase duration of dexamethasone release. We found that 0 to 10% of croscarmellose ranges afforded a 6 week release profile, while 0 to 5% further increased release up to 12 months. In contrast, 15-25% croscarmellose ranges yielded a shorter 2 week release profile, although 20 to 25% was also useful.

It should be understood that the above-described arrangements are only illustrative of application of the principles of the present invention. Numerous modifications and alternative arrangements may be devised by those skilled in the art without departing from the spirit and scope of the present invention. Thus, while the present invention has been described above with particularity and detail in connection with what is presently deemed to be the most practical and preferred embodiments of the invention, it will be apparent to those of ordinary skill in the art that numerous modifications, including, but not limited to, variations in size, materials, shape, form, function and manner of operation, assembly and use may be made without departing from the principles and concepts set forth herein.

What is claimed is:

1. An intraocular active agent delivery device, comprising:
   an active agent homogenously combined with a biodegradable active agent matrix such that the entire delivery device is homogenous, said homogenous delivery device having a shape and size to fit within a lens capsule of an eye and provide a therapeutically effective amount of the active agent to the eye, said active agent consisting of dexamethasone and optionally an antibiotic, an NSAID, or a combination thereof for treatment of inflammation post-cataract surgery, and said biodegradable active agent matrix being formulated to provide sustained release of the therapeutically effective amount of the active agent during a release period.

2. The device of claim 1, wherein the active agent is present in the biodegradable active agent matrix in an amount from about 5 wt % to about 50 wt %.

3. The device of claim 1, wherein the release period is from about 2 weeks to about 8 weeks.

4. The device of claim 1, wherein the sustained release of the therapeutically effective amount of the active agent is provided to both the anterior and posterior segments of the eye.

5. The device of claim 1, wherein the biodegradable active agent matrix comprises at least one of poly(lactic-co-glycolide), polylactic-polyglycolic acid block copolymers (PLGA), hydroxypropyl methyl cellulose (HPMC), hydroxyl methyl cellulose, polyglycolide-polyvinyl alcohol, hydroxypropylcellulose, sodium carboxymethylcellulose, polylactic acid (PLA), polyglycolic acid (PGA) polyglycolic acid-polyvinyl alcohol block copolymers (PGA/PVA), hydroxypropylmethylcellulose (HPMC), polycaprolactone (PCL), and polycaprolactone-polyethylene glycol block copolymers.

6. The device of claim 1, wherein the biodegradable active agent matrix comprises poly(lactic-co-glycolide) having a copolymer ratio from about 60/40 to about 40/60.

7. The device of claim 1, wherein the biodegradable active agent matrix further comprises a disintegrant.

8. The device of claim 7, wherein the disintegrant is croscarmellose, or a salt thereof.

9. The device of claim 1, wherein the device is in the form of a suspension or dispersion of the active agent within a biodegradable polymer matrix precursor, the biodegradable polymer matrix precursor forming the biodegradable active agent matrix in situ.

10. The device of claim 1, wherein the delivery device has a total mass of 0.2 mg to 4 mg.

11. The device of claim 1, wherein the biodegradable active agent matrix is shaped as a crescent, disc, rod, or pellet.

12. The device of claim 11, wherein the disc or pellet has a diameter ranging from about 0.4 mm to about 3 mm and a thickness ranging from about 0.2 mm to about 2 mm.

13. The device of claim 11, wherein the biodegradable active agent matrix is shaped as a rod.

14. The device of claim 13, wherein the rod has a diameter ranging from about 0.05 mm to about 2 mm and a length ranging from about 0.5 mm to about 5 mm.

15. The device of claim 1, wherein the delivery device is formulated to biodegrade at a rate to release on average from 1 mcg to 12 mcg per day of the active agent during the release period.

16. The device of claim 1, wherein the delivery device is formulated to biodegrade to release from 100 mcg to 400 mcg of the active agent during the release period.

17. A method of treating an eye condition, comprising:
   inserting an intraocular active agent delivery device into the lens capsule of an eye either during or after a cataract surgery, said intraocular drug delivery device including an active agent homogenously combined with a biodegradable active agent matrix such that the entire delivery device is homogenous, said homogenous delivery device having a shape and size to provide a therapeutically effective amount of the active agent to the eye, said active agent consisting of dexamethasone and optionally an antibiotic, an NSAID, or a combination thereof, and said biodegradable active agent matrix being formulated to provide sustained release of a therapeutically effective amount of the active agent during a release period; and allowing the biodegradable active agent matrix to biodegrade to provide sustained release of the therapeutically effective amount of the active agent to the eye during the release period to treat inflammation.

18. The method of claim 17, wherein the eye condition is uveitis.

19. The method of claim 17, wherein the release period is from 2 weeks to 8 weeks.

20. The method of claim 17, wherein the biodegradable active agent matrix biodegrades to provide from 100 mcg to 400 mcg of the active agent during the release period.

21. The method of claim 17, wherein the biodegradable active agent matrix biodegrades at a rate to provide on average from 1 mcg to 12 mcg per day of the active agent during the release period.

22. The method of claim 17, wherein the sustained release of the active agent reduces retinal thickening associated with the ocular condition as compared to retinal thickening without treatment.

23. The method of claim 22, wherein retinal thickness is reduced by at least 10 μm within a period of 2 weeks after inserting the intraocular active agent delivery device as compared to retinal thickness without treatment.

\* \* \* \* \*